US008916683B2

(12) United States Patent
Olsen et al.

(10) Patent No.: US 8,916,683 B2
(45) Date of Patent: Dec. 23, 2014

(54) NANOSTRUCTURED PHYSICALLY-ASSOCIATING HYDROGELS FOR INJECTABLE, RESPONSIVE, AND TOUGH BIOMATERIALS

(75) Inventors: Bradley D. Olsen, Arlington, MA (US); Matthew J. Glassman, Cambridge, MA (US); Jacqueline Chan, Arcadia, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 474 days.

(21) Appl. No.: 13/253,485

(22) Filed: Oct. 5, 2011

(65) Prior Publication Data
US 2014/0024722 A1    Jan. 23, 2014

Related U.S. Application Data

(60) Provisional application No. 61/389,765, filed on Oct. 5, 2010.

(51) Int. Cl.
| | | |
|---|---|---|
| *A61K 47/42* | (2006.01) | |
| *C07K 2/00* | (2006.01) | |
| *C07K 14/00* | (2006.01) | |
| *A61L 27/22* | (2006.01) | |
| *A61L 27/52* | (2006.01) | |

(52) U.S. Cl.
CPC .............. *A61K 47/42* (2013.01); *A61L 27/227* (2013.01); *A61L 27/52* (2013.01)
USPC ........ 530/345; 424/78.17; 424/486; 424/487; 525/54.1; 530/408

(58) Field of Classification Search
None
See application file for complete search history.

(56) References Cited

U.S. PATENT DOCUMENTS

| | | | |
|---|---|---|---|
| 5,712,366 A | 1/1998 | McGrath et al. | |
| 6,090,911 A * | 7/2000 | Petka et al. | 530/300 |
| 7,691,366 B2 | 4/2010 | Koh | |
| 2009/0075335 A1* | 3/2009 | Banta et al. | 435/69.1 |
| 2009/0170959 A1* | 7/2009 | Montclare et al. | 514/773 |
| 2012/0202263 A1* | 8/2012 | Blakely et al. | 435/188 |

OTHER PUBLICATIONS

Kopecek et al. Hydrogels as smart biomaterials. Polymer International. 2007, vol. 56, pp. 1078-1098.*
Mann et al. Smooth muscle cell growth in photopolymerized hydrogels . . . Biomaterials. 2001, vol. 22, pp. 3045-3051.*
Chung et al., "Engineering Cartilage Tissue," Advanced Drug Delivery Reviews, 60(2):243-262 (2008).
Gong et al., "Double-Network Hydrogels with Extremely High Mechanical Strength," Advanced Materials, 15(14):1155-1158 (2003).
Henderson et al., "Ionically Cross-Linked Triblock Copolymer Hydrogels with High Strength," Macromolecules, 43(14):6193-6201 (2010).

(Continued)

*Primary Examiner* — Jeffrey E Russel
(74) *Attorney, Agent, or Firm* — Dana M. Gordon; Foley Hoag LLP

(57) ABSTRACT

Described herein are block copolymer conjugates that form double-network hydrogels under appropriate conditions. The conjugates comprise a block of polymer end-group, a block of self-associating peptide or protein, and flexible linkers between the two. Hydrogels comprising the conjugates have the mechanical properties, including elastic modulus and fracture toughness, required for load-bearing applications, while maintaining desirable shear-thinning properties, for example, for injectability.

22 Claims, 19 Drawing Sheets

(56) References Cited

OTHER PUBLICATIONS

Lim et al., "In Situ Cross-Linking of Elastin-like Polypeptide Block Copolymers for Tissue Repair," Biomacromolecules, 9:222-230 (2008).

Olsen et al., "Yielding Behavior in Injectable Hydrogels from Telechelic Proteins," Macromolecules, 43(21):9094-9099 (2010).

Seitz et al., "Micelle Morphology and Mechanical Response of Triblock Gels," Macromolecules, 42(22):9133-9140 (2009).

Xu, Chunyu, "Protein-Based Hydrogels Self-Assembled from Genetically Engineered Triblock Polypeptides Containing Coiled-Coil Domains," Dissertation, University of Utah, Aug. 2006.

International Search Report dated Apr. 30, 2012, from PCT/US2011/054937.

* cited by examiner

E  C  P 80 kDa
60 kDa
50 kDa
40 kDa

FT  W  E

PNIPAM synthetic scheme

P = APQMLRELQETNAALQDVRELLRQQVKEITFLKNTVMESDAS
C₁₀ = [AGAGAGPEG]₁₀

NANOSTRUCTURED PHYSICALLY-ASSOCIATING HYDROGELS FOR INJECTABLE, RESPONSIVE, AND TOUGH BIOMATERIALS

RELATED APPLICATIONS

This application claims the benefit of priority to U.S. Provisional Patent Application Ser. No. 61/389,765, filed Oct. 5, 2010, the contents of which are hereby incorporated by reference.

GOVERNMENT SUPPORT

This invention was made with Government support under Grant No. W911NF-07-D-0004, awarded by the Army Research Office. The Government has certain rights in this invention.

BACKGROUND

Overview

Hydrogels are an important platform technology for biomedical solutions in many areas, including managing chronic ailments, such as rheumatoid arthritis and osteoporosis, and treating acute conditions, such as hemorrhaging and cancer. Their utility is due in part to their high water content and tunable mechanical properties, which makes them inherently similar to living tissue. Hydrogels have been widely investigated for contact lenses, as scaffolds for load-bearing connective tissue, and as materials for controlled drug release. Their demonstrated mechanical behavior spans a broad spectrum of useful properties: chemically crosslinked double-network hydrogels exhibit high toughness, and physically crosslinked protein-based hydrogels can shear-thin and are well suited for injectable biomaterials. This latter property is particularly promising in the clinical setting because the ability to implant a solid formulation using a minimally-invasive technique can enable superior control in the delivery of drugs and cellular materials.

A variety of injectable hydrogel formulations have been developed, such as those that rely on responsive chemical crosslinking or physical association triggered in the physiological environment. Shear-thinning gels are particularly useful due to their ability to achieve full elastic strength rapidly after injection and promote the survival of encapsulated cells due to plug flow profiles during injection. Unfortunately, current shear-thinning gels do not meet the requirements for elastic modulus and fracture toughness required for load-bearing applications, and there is no method to prevent shear-thinning after injection. To maintain injectability during processing and ultimately achieve the mechanical properties desired at the implantation site, a responsive toughening mechanism for shear-thinning hydrogels is needed.

Protein-Based Physical Hydrogels as Injectable Biomaterials

Genetic engineering and biosynthesis provide a route to the facile design and production of polymers with precisely determined sequences, and these tools have been leveraged in the engineering of a number of useful materials for sensing, responsive drug delivery, and catalysis. A variety of naturally occurring protein sequences have been utilized in physical hydrogels, including coiled-coil associating domains and elastin-based polypeptides exhibiting lower critical solution temperatures. In the case of proteins incorporating coiled-coil domains, precise sequence control allows gels to be prepared with enhanced control over network topology. Depending on their amino acid sequence, these alpha-helical domains will associate in either parallel or anti-parallel directions and do so with well-defined valencies. When linked together by flexible chains, either structure-less polyelectrolyte protein domains or poly(ethylene glycol), they reversibly associate to form a network. Thus, preparing hydrogels with different coiled-coils or different sized linker domains provides a handle on the material's mechanical properties and degradation rates.

A well-studied coiled-coil-based gel is composed of helices that associate in pentameric bundles (abbreviated P) connected by 10 repeat units of a structure-less nonapeptide linker sequence (abbreviated C). The linker sequences can be modified to include cell binding peptides without sacrificing the mechanical properties of the gel, providing a useful mechanism for engineering biofunctionality. $PC_{10}P$ gels prepared at a 7% (w/v) concentration have elastic moduli near 4 kPa, typical for physically associating gels. The material is responsive to pH and thermal changes that cause the protein to unfold, but these responsive transitions are typically outside of physiological ranges. At large strain the gels exhibit a yield response indicative of rapid shear-thinning behavior, and recovery of the elastic modulus is almost instantaneous following cessation of shear. Velocity profiles observed in capillary flow have plug flow character due to shear banding near the boundaries. Because of this localization of strain, hydrogel formulations encapsulating cells sustain high survival rates post-injection. Similar success in cell survivability has been achieved in other peptide-based hydrogels, although in this example the recovery of the elastic modulus was on the order of minutes.

Gel Toughening

One method for the toughening of hydrogels is the incorporation of dispersed domains of stiff material, as in clay or carbon nanotube (CNT) nanocomposites. These materials have tremendous promise to enhance mechanical properties—such as elastic modulus—at low loadings, and they are compatible with typical polymer processing techniques. In the case of CNT nanocomposites, the slow progress in achieving the desired enhancement has been due to the difficulty of producing molecularly disperse composites. For CNTs and other materials used in nanocomposites, aggregated clusters can lead to lower surface areas and higher flexibility of the filler material, reducing the expected reinforcement effect. Although surface functionalization has been used to attempt to resolve this issue, care must be taken such that the chemical processing does not compromise the morphology of the filler.

Double network hydrogels represent an alternative means to achieve toughened gels, and they have had great success approaching the elastic modulus and fracture properties of articular cartilage. These gels consist of two independent, interpenetrating networks typically of different chemical nature and connected over different length scales. Such materials can exhibit an order of magnitude improvement in elastic moduli up to tens of MPa and stresses at fracture up to 20 times that of a single network of either one of the component polymers. A large mismatch in monomer feed ratios and crosslinking densities is important to achieve optimal enhancement. Optical interference measurements on compression studies show that optimized double-network gels exhibit weak birefringence compared to sub-optimal formulations. These data suggest that stresses are effectively distributed throughout the material, with the loosely crosslinked network dissipating localized stresses and preventing crack growth in the material.

While the above strategies provide valuable lessons on engineering toughness in soft materials, neither has been suitably adapted for use in injectable biomaterials, which require toughening mechanisms that can be activated after implantation, when flow behavior is no longer needed. High performance clay nanocomposites and double-network hydrogels have been prepared from chemical gels, so responsive crosslinking of a liquid formulation has been proposed to meet these constraints. However, responsive chemical gels typically have higher cytotoxicity and slower curing times than shear-thinning physical gels.

Two approaches have been taken to responsively toughen physical hydrogels. Recently, a protein-based physical hydrogel has been strengthened via photo-initiated chemical crosslinking to give approximately a three-fold improvement in the elastic modulus. However, even the crosslinked material is insufficient for use in load-bearing tissues. Additionally, photoirradiation of an implanted material can be complicated in the clinical setting due to limited tissue penetration of the radiation, and the toxicity of residual crosslinking agents must be taken into account. The modulus of a triblock-copolymer hydrogel was increased by over two orders of magnitude by crosslinking the polyanionic midblock with divalent inorganic cations. While this work demonstrates that the double-network principle can be implemented using two physical networks, crosslinking with diffusible ions is unsuitable for many biomedical applications. The material would equilibrate with the local tissue environment, likely losing some of the enhancement in mechanical performance. Furthermore, the processing required to achieve enhanced toughness is not readily adapted to the clinical setting, and the response time is 12-72 hours.

Much progress has been made in the toughening of soft materials, but no single strategy has succeeded in simultaneously satisfying the demands of injectable biomaterials, namely pressure-driven flow through narrow geometries, rapid restoration of solid-like behavior after the cessation of shear, responsive toughening, and biocompatibility. Nevertheless, lessons from the design of double-network chemical gels—the interpenetration of a stiff but brittle network with a soft but ductile network—can inform the design of responsively tough, injectable biomaterials.

SUMMARY OF THE INVENTION

In certain embodiments, the invention relates to a conjugate comprising a block copolymer of structure $AB(DB)_xA$, wherein
D comprises an associating group, wherein the associating group comprises a sequence of amino acids;
B represents a flexible linker group, wherein the flexible linker group is hydrophilic;
A represents a polymeric end-group; and
x is 1, 2, 3, 4, 5, 6, 7, 8, 9, or 10.
In certain embodiments, the invention relates to a hydrogel comprising any one of the above-mentioned conjugates; and a buffered aqueous solution.

BRIEF DESCRIPTION OF THE FIGURES

FIG. 10(b) discloses "P" as SEQ ID NO: 13 and "$C_{10}$" as SEQ ID NO: 7.

DETAILED DESCRIPTION

Overview

Figure 1:
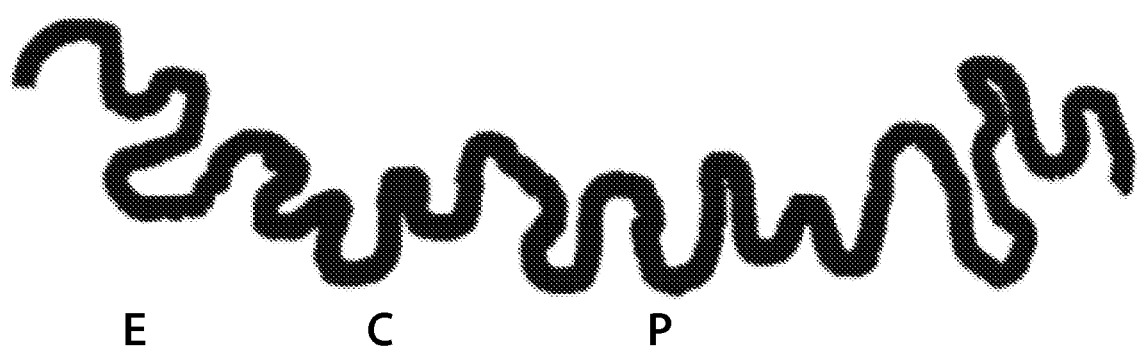
FIG. 1 depicts a cartoon of a multi-block copolymer incorporating two independent physically-associating groups: E (or A) and P (or D). Flexible chains, C (or B), form covalent linkages between the associating groups.

In certain embodiments, the invention relates to a method for controlling mechanical properties in physical hydrogels through the engineering of two independent physically responsive networks within a single molecule to produce systems of physical double network hydrogels. In certain embodiments, the independence of the two networks allows the characteristic length scales and relaxation times of each network to be engineered independently and provides a system that is responsive to two stimuli. In certain embodiments, the components necessary for association in both networks are covalently attached to the gel-forming molecule, enabling gelation under a wide variety of solution conditions.

In certain embodiments, the invention relates to a conjugate comprising small associating groups and large associating endgroups, wherein the two associating systems are differentiated in that the endgroups associate on a larger length scale than the small associating groups. In certain embodiments, the conjugate further comprises flexible linker groups between a plurality of small associating groups. In certain embodiments, the flexible linker groups are soluble in the solvent that is to be gelled. In certain embodiments, the solvent to be gelled is water, thereby forming a hydrogel. In certain embodiments, the small specifically associating groups form physical associations directly with one another through hydrophobic interactions, hydrogen bonding, or ionic interactions. In certain embodiments, the small associating groups form clusters where the number of associating groups and their spatial arrangement in the cluster is controlled by the chemical design of the molecule. In certain embodiments, the large associating endgroups associate due to interactions that are orthogonal to those of the small associating groups, such that the grafts and the small associating groups form spatially separate aggregates, and both associating interactions may be formed or broken separately. In certain embodiments, the strength of interactions between both small associating groups and large polymer grafts may be responsive to pH, temperature, or ionic strength.

In certain embodiments, the invention relates to a conjugate having a linear architecture with two identical end blocks (E or A) that form the first network, and a midblock containing a variable number of interior associating groups (P or D). In certain embodiments, each associating group is connected by a flexible chain (C or B) which is water-soluble.

In certain embodiments, the invention relates to a conjugate that forms a solid gel at and below biologically relevant temperatures (i.e., about 37° C.) due to specific association of the P domains. In certain embodiments, the conjugates retain the ability to be injected due to strong shear-thinning flow. In certain embodiments, the conjugates rapidly self-heal by reassociation of the P domains. In certain embodiments, heating the conjugate to about 37° C. results in the assembly of the large length scale network of endblocks, enhancing the toughness and elastic modulus of the network.

Exemplary Conjugates of the Invention

In certain embodiments, the invention relates to a conjugate comprising a triblock copolymer. In certain embodiments, one block of the triblock copolymer comprises an associating group (P or D). In certain embodiments, the associating group is a coiled-coil protein. In certain embodiments, the associating group is a protein. In certain embodiments, the associating group is a protein consisting of a sequence of about 43 amino acids that forms a strong homopentameric interaction. In certain embodiments, one block of the triblock copolymer comprises a flexible linker (C or B). In certain embodiments, the flexible linker is a protein. In certain embodiments, the flexible linker is a protein consisting of a sequence of about 90 amino acids. In certain embodiments, one block of the triblock copolymer comprises the endgroups (E or A). In certain embodiments, the end-groups comprise a synthetic polymer. In certain embodiments, the end-groups comprise a polymer made from N-isopropylacrylamide (NIPAM) or N-tert-butylacrylamide (tBAM). In certain embodiments, the end-groups comprise a protein. In certain embodiments, the end-groups comprise an engineered protein. In certain embodiments, the P (or D) network can be switched on or off at biologically extreme temperatures and pHs that will denature the protein blocks, while the E (or A) network can be toggled at biologically relevant temperatures that trigger the lower critical solution phenomenon at about 30° C.

In certain embodiments, the invention relates to a conjugate comprising a block copolymer of structure $AB(DB)_xA$, wherein D comprises an associating group, wherein the associating group comprises a sequence of amino acids;

B represents a flexible linker group, wherein the flexible linker group is hydrophilic;

A represents a polymeric end-group; and x is 1, 2, 3, 4, 5, 6, 7, 8, 9, or 10.

In certain embodiments, the invention relates to any one of the aforementioned conjugates, wherein D is a sequence of from about 30 to about 55 amino acids.

In certain embodiments, the invention relates to any one of the aforementioned conjugates, wherein D is a sequence of about 35, about 36, about 37, about 38, about 39, about 40, about 41, about 42, about 43, about 44, about 45, or about 46 amino acids.

In certain embodiments, the invention relates to any one of the aforementioned conjugates, wherein D is a sequence of about 43 amino acids.

In certain embodiments, the invention relates to any one of the aforementioned conjugates, wherein D is represented by a sequence having at least 85% sequence homology to APQM-LRELQETNAALQDVRELLRQQVKEIT-FLKNTVMESDASG (SEQ ID NO: 2).

In certain embodiments, the invention relates to any one of the aforementioned conjugates, wherein D is represented by a sequence having at least 90% sequence homology to APQM-LRELQETNAALQDVRELLRQQVKEIT-FLKNTVMESDASG (SEQ ID NO: 2).

In certain embodiments, the invention relates to any one of the aforementioned conjugates, wherein D is represented by a sequence having at least 95% sequence homology to APQM-LRELQETNAALQDVRELLRQQVKEIT-FLKNTVMESDASG (SEQ ID NO: 2).

In certain embodiments, the invention relates to any one of the aforementioned conjugates, wherein D is represented by a sequence having at least 98% sequence homology to APQM-LRELQETNAALQDVRELLRQQVKEIT-FLKNTVMESDASG (SEQ ID NO: 2).

In certain embodiments, the invention relates to any one of the aforementioned conjugates, wherein D is represented by a sequence having at least 99% sequence homology to APQM-LRELQETNAALQDVRELLRQQVKEIT-FLKNTVMESDASG (SEQ ID NO: 2).

In certain embodiments, the invention relates to any one of the aforementioned conjugates, wherein D is represented by a sequence having at least 85% sequence homology to QHIEKSVEEIDEELAKLEEQIKILQTKIEGLVGRHPDLT (SEQ ID NO: 3).

In certain embodiments, the invention relates to any one of the aforementioned conjugates, wherein D is represented by a sequence having at least 90% sequence homology to QHIEKSVEEIDEELAKLEEQIKILQTKIEGLVGRHPDLT (SEQ ID NO: 3).

In certain embodiments, the invention relates to any one of the aforementioned conjugates, wherein D is represented by a sequence having at least 95% sequence homology to QHIEKSVEEIDEELAKLEEQIKILQTKIEGLVGRHPDLT (SEQ ID NO: 3).

In certain embodiments, the invention relates to any one of the aforementioned conjugates, wherein D is represented by a sequence having at least 98% sequence homology to QHIEKSVEEIDEELAKLEEQIKILQTKIEGLVGRHPDLT (SEQ ID NO: 3).

In certain embodiments, the invention relates to any one of the aforementioned conjugates, wherein D is represented by a sequence having at least 99% sequence homology to QHIEKSVEEIDEELAKLEEQIKILQTKIEGLVGRHPDLT (SEQ ID NO: 3).

In certain embodiments, the invention relates to any one of the aforementioned conjugates, wherein D is represented by a sequence having at least 85% sequence homology to QHIEKSVEEIDEELAKLEEQKKILQT-KREGLVGRHPDLT (SEQ ID NO: 4).

In certain embodiments, the invention relates to any one of the aforementioned conjugates, wherein D is represented by a sequence having at least 90% sequence homology to QHIEKSVEEIDEELAKLEEQKKILQT-KREGLVGRHPDLT (SEQ ID NO: 4).

In certain embodiments, the invention relates to any one of the aforementioned conjugates, wherein D is represented by a sequence having at least 95% sequence homology to QHIEKSVEEIDEELAKLEEQKKILQT-KREGLVGRHPDLT (SEQ ID NO: 4).

In certain embodiments, the invention relates to any one of the aforementioned conjugates, wherein D is represented by a sequence having at least 98% sequence homology to QHIEKSVEEIDEELAKLEEQKKILQT-KREGLVGRHPDLT (SEQ ID NO: 4).

In certain embodiments, the invention relates to any one of the aforementioned conjugates, wherein D is represented by a sequence having at least 99% sequence homology to QHIEKSVEEIDEELAKLEEQKKILQT-KREGLVGRHPDLT (SEQ ID NO: 4).

In certain embodiments, the invention relates to any one of the aforementioned conjugates, wherein D is represented by a sequence having at least 85% sequence homology to SGDLENEVAQLEREVRSLE-DEAAELEQKVSRLKNEIEDLKAE (SEQ ID NO: 5).

In certain embodiments, the invention relates to any one of the aforementioned conjugates, wherein D is represented by a sequence having at least 90% sequence homology to SGDLENEVAQLEREVRSLE-DEAAELEQKVSRLKNEIEDLKAE (SEQ ID NO: 5).

In certain embodiments, the invention relates to any one of the aforementioned conjugates, wherein D is represented by a sequence having at least 95% sequence homology to SGDLENEVAQLEREVRSLE-DEAAELEQKVSRLKNEIEDLKAE (SEQ ID NO: 5).

In certain embodiments, the invention relates to any one of the aforementioned conjugates, wherein D is represented by a sequence having at least 98% sequence homology to SGDLENEVAQLEREVRSLE-DEAAELEQKVSRLKNEIEDLKAE (SEQ ID NO: 5).

In certain embodiments, the invention relates to any one of the aforementioned conjugates, wherein D is represented by a sequence having at least 99% sequence homology to SGDLENEVAQLEREVRSLE-DEAAELEQKVSRLKNEIEDLKAE (SEQ ID NO: 5).

In certain embodiments, the invention relates to any one of the aforementioned conjugates, wherein D does not comprise a cysteine residue.

In certain embodiments, the invention relates to any one of the aforementioned conjugates, wherein D is a sequence of amino acids that forms a homodimer, a homotrimer, a homotetramer, or a homopentamer.

In certain embodiments, D is a homodimeric coiled-coil that associates in parallel or antiparallel orientations. In certain embodiments, D is a homotetrameric coiled-coil that associates in an antiparallel orientation.

In certain embodiments, the invention relates to any one of the aforementioned conjugates, wherein B is a sequence of amino acids.

In certain embodiments, the invention relates to any one of the aforementioned conjugates, wherein B is a sequence of from about 70 to about 110 amino acids.

In certain embodiments, the invention relates to any one of the aforementioned conjugates, wherein B is a sequence of about 90 amino acids.

In certain embodiments, the invention relates to any one of the aforementioned conjugates, wherein B comprises a sequence of amino acids; and the sequence of amino acids is AGAGAGPEG (SEQ ID NO: 6).

In certain embodiments, the invention relates to any one of the aforementioned conjugates, wherein B is represented by a sequence having at least 85% sequence homology to [AGAGAGPEG]$_{10}$ (SEQ ID NO: 7).

In certain embodiments, the invention relates to any one of the aforementioned conjugates, wherein B is represented by a sequence having at least 90% sequence homology to [AGAGAGPEG]$_{10}$ (SEQ ID NO: 7).

In certain embodiments, the invention relates to any one of the aforementioned conjugates, wherein B is represented by a sequence having at least 95% sequence homology to [AGAGAGPEG]$_{10}$ (SEQ ID NO: 7).

In certain embodiments, the invention relates to any one of the aforementioned conjugates, wherein B is represented by a sequence having at least 98% sequence homology to [AGAGAGPEG]$_{10}$ (SEQ ID NO: 7).

In certain embodiments, the invention relates to any one of the aforementioned conjugates, wherein B is represented by a sequence having at least 99% sequence homology to [AGAGAGPEG]$_{10}$ (SEQ ID NO: 7).

In certain embodiments, the invention relates to any one of the aforementioned conjugates, wherein B does not comprise a cysteine residue.

In certain embodiments, the invention relates to any one of the aforementioned conjugates, wherein B is absent.

In certain embodiments, the invention relates to any one of the aforementioned conjugates, wherein A is a polymer made from a monomer selected from the group consisting of: N-isopropylacrylamide, N-tert-butylacrylamide, N-isobutylacrylamide, N-octylacrylamide, hydroxypropylacrylate, hydroxyethylacrylate, hydroxymethylacrylate, ethylene glycol acrylate, oligo(ethylene glycol) acrylate, N-isopropylmethacrylamide, methyl methacrylate, ethyl methacrylate, n-propyl methacrylate, isopropyl methacrylate, isobutyl methacrylate, t-butyl methacrylate, methyl 2-furanacrylate, benzyl 2-furanacrylate, vinyl acetate, and stearyl methacrylate, and combinations thereof.

In certain embodiments, the invention relates to any one of the aforementioned conjugates, wherein A is a polymer made from a monomer selected from the group consisting of: N-isopropylacrylamide, N— tert-butylacrylamide, N-isobutylacrylamide, N-octylacrylamide, hydroxypropylacrylate, hydroxyethylacrylate, hydroxymethylacrylate, ethylene glycol acrylate, oligo(ethylene glycol) acrylate, N-isopropylmethacrylamide, and combinations thereof.

In certain embodiments, the invention relates to any one of the aforementioned conjugates, wherein A is a polymer made from a monomer selected from the group consisting of: N-isopropylacrylamide, N-tert-butylacrylamide, N-isobutylacrylamide, N-octylacrylamide, and combinations thereof.

In certain embodiments, the invention relates to any one of the aforementioned conjugates, wherein A is a polymer made from N-isopropylacrylamide.

In certain embodiments, the invention relates to any one of the aforementioned conjugates, wherein A is a polymer made from N-isopropylacrylamide and t-butylacrylamide.

In certain embodiments, the invention relates to any one of the aforementioned conjugates, wherein A is a polymer made from about 75% N-isopropylacrylamide and about 25% t-butylacrylamide.

In certain embodiments, the invention relates to any one of the aforementioned conjugates, wherein A is a protein.

In certain embodiments, the invention relates to any one of the aforementioned conjugates, wherein A is an engineered protein.

In certain embodiments, the invention relates to any one of the aforementioned conjugates, wherein A comprises a sequence of amino acids; the sequence of amino acids comprises a five-amino acid repeat unit; the five-amino acid repeat unit is VPGXG; and X is any amino acid (SEQ ID NO: 8).

In certain embodiments, the invention relates to any one of the aforementioned conjugates, wherein A comprises a sequence of amino acids; the sequence of amino acids comprises a five-amino acid repeat unit; the five-amino acid repeat unit is VPGXG; and X is alanine or glycine (SEQ ID NO: 9).

In certain embodiments, the invention relates to any one of the aforementioned conjugates, wherein A comprises a sequence of amino acids; the sequence of amino acids is VPAVG(IPAVG)$_4$ (SEQ ID NO: 10).

In certain embodiments, the invention relates to any one of the aforementioned conjugates, wherein A comprises a sequence of amino acids; the sequence of amino acids is [VPAVG(IPAVG)$_4$]$_n$; and n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 (SEQ ID NO: 11).

In certain embodiments, the invention relates to any one of the aforementioned conjugates, wherein A comprises a sequence of amino acids; the sequence of amino acids is [VPAVG(IPAVG)$_4$]$_n$; and n is 1, 2, 3, 4, 5, 6, 7, 8, 9, or 10 (SEQ ID NO: 12).

In certain embodiments, the invention relates to any one of the aforementioned conjugates, wherein A is represented by a sequence of amino acids having at least 85% sequence homology to [VPAVG(IPAVG)$_4$]$_n$; and n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 (SEQ ID NO: 11).

In certain embodiments, the invention relates to any one of the aforementioned conjugates, wherein A is represented by a sequence of amino acids having at least 90% sequence homology to [VPAVG(IPAVG)$_4$]$_n$; and n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 (SEQ ID NO: 11).

In certain embodiments, the invention relates to any one of the aforementioned conjugates, wherein A is represented by a sequence of amino acids having at least 95% sequence homology to [VPAVG(IPAVG)$_4$]$_n$; and n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 (SEQ ID NO: 11).

In certain embodiments, the invention relates to any one of the aforementioned conjugates, wherein A is represented by a sequence of amino acids having at least 98% sequence homology to [VPAVG(IPAVG)$_4$]$_n$; and n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 (SEQ ID NO: 11).

In certain embodiments, the invention relates to any one of the aforementioned conjugates, wherein A is represented by a sequence of amino acids having at least 99% sequence homology to [VPAVG(IPAVG)$_4$]$_n$; and n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 (SEQ ID NO: 11).

In certain embodiments, the invention relates to any one of the aforementioned conjugates, wherein A is hydrophobic.

In certain embodiments, the invention relates to any one of the aforementioned conjugates, wherein A exhibits lower critical solution behavior than D.

In certain embodiments, the invention relates to any one of the aforementioned conjugates, wherein the number average molecular weight of A is from about 8 kDa to about 50 kDa.

In certain embodiments, the invention relates to any one of the aforementioned conjugates, wherein the number average molecular weight of A is about 10 kDa, about 15 kDa, about 20 kDa, about 25 kDa, about 30 kDa, about 35 kDa, about 40 kDa, or about 45 kDa.

In certain embodiments, the invention relates to any one of the aforementioned conjugates, wherein the polydispersity of A is less than about 1.5, less than about 1.4, less than about 1.3, less than about 1.2, or less than about 1.1.

In certain embodiments, the invention relates to any one of the aforementioned conjugates, further comprising a linker between B and A.

In certain embodiments, the invention relates to any one of the aforementioned conjugates, further comprising a thiol-maleimide linker between B and A.

In certain embodiments, the invention relates to any one of the aforementioned conjugates, further comprising a linker between B and A, wherein the linker comprises the following structure:

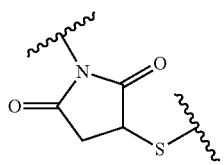

In certain embodiments, the invention relates to any one of the aforementioned conjugates, further comprising a linker between B and A, wherein the linker is represented by the following structure:

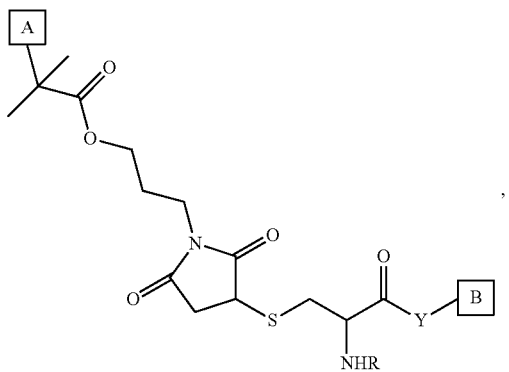

wherein
R represents —H or an amino acid; and
Y is absent or is an amino acid.

In certain embodiments, the invention relates to any one of the aforementioned conjugates, further comprising a histidine tag.

In certain embodiments, the invention relates to any one of the aforementioned conjugates, wherein B is a sequence of amino acids; and the conjugate further comprises a histidine tag between A and the N-terminus of B.

In certain embodiments, the invention relates to any one of the aforementioned conjugates, wherein B is a sequence of amino acids; and the conjugate further comprises about six histidine residues between A and the N-terminus of B.

In certain embodiments, the invention relates to any one of the aforementioned conjugates, wherein x is 1, 2, 3, or 4.

In certain embodiments, the invention relates to any one of the aforementioned conjugates, wherein x is 1.

In certain embodiments, the invention relates to any one of the aforementioned conjugates, wherein x is 2.

In certain embodiments, the invention relates to any one of the aforementioned conjugates, wherein x is 3.

In certain embodiments, the invention relates to any one of the aforementioned conjugates, wherein x is 4.

Exemplary Hydrogels of the Invention

In certain embodiments, the invention relates to a hydrogel comprising any one of the aforementioned conjugates; and a buffered aqueous solvent.

In certain embodiments, the invention relates to any one of the aforementioned hydrogels, wherein polymeric end-groups are associated with other polymeric end-groups, thereby forming a polymeric end-group network; and associating groups are associated with other associating groups, thereby forming an associating group network.

In certain embodiments, the invention relates to any one of the aforementioned hydrogels, wherein the polymeric end-groups associate with each other on a larger length scale than the associating groups; the polymeric end-groups and the associating groups form spatially separate aggregates; and the hydrogel is a physical double network hydrogel.

In certain embodiments, the invention relates to any one of the aforementioned hydrogels, wherein the length scale and relaxation time of the polymeric end-group network are responsive to a first stimulus; the length scale and the relaxation time of the associating group network are responsive to a second stimulus; and the hydrogel is responsive to two stimuli.

In certain embodiments, the invention relates to any one of the aforementioned hydrogels, wherein the first stimulus or the second stimulus is a change in temperature.

In certain embodiments, the invention relates to any one of the aforementioned hydrogels, wherein the hydrogel is a solid at about 37° C. under substantially no shear.

In certain embodiments, the invention relates to any one of the aforementioned hydrogels, wherein the hydrogel is a liquid under a substantial amount of shear.

Exemplary Methods of the Invention

In certain embodiments, the invention relates to a method of synthesizing any one of the aforementioned conjugates or hydrogels. In certain embodiments, the conjugate is synthesized in two components that are linked together in a final step.

In certain embodiments, the associating group (P or D) is synthesized biologically in $E.$ $coli$ and purified from the cell lysate by affinity chromatography or selective precipitation using chaotropic salts. In certain embodiments, the conjugate comprises an alternating arrangement of flexible linker domains (B or $C_{10}$) and associating domains (P or D). In certain embodiments, the gene is subcloned into a pQE9 expression system. In certain embodiments, purification is performed under reducing conditions by the addition of 10 mM 2-mercaptoethanol in all buffers. In certain embodiments, the $B(DB)_x$ protein is recovered as a lyophilized powder.

Figure 3:
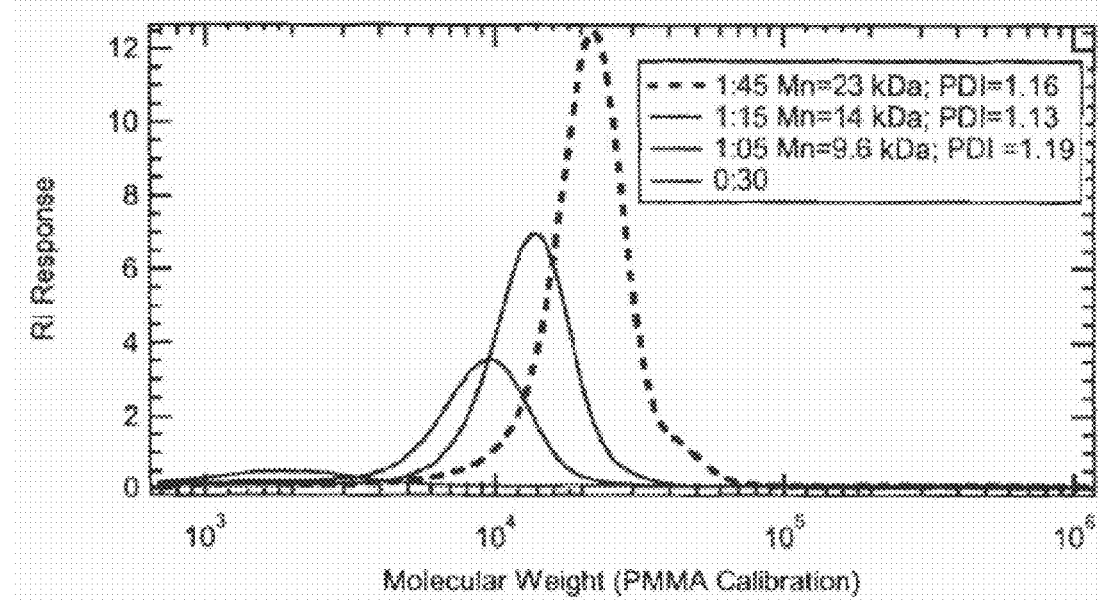
FIG. 3 depicts GPC traces of monodisperse PNIPAM produced via RAFT. Legend is labeled with the timepoint at which the reaction was sampled, the number-averaged molecular weight ($M_n$) and the polydispersity index (PDI).

In certain embodiments, the PNIPAM endblocks are synthesized via Reversible Addition-Fragmentation Chain Transfer (RAFT) polymerization, a controlled living free radical polymerization technique that gives monodisperse polymers (FIG. 3). In certain embodiments, a typical polymerization reaction targeting a molecular weight of approximately 30 kDa is performed in acetonitrile at a 2.0 M concentration of N-isopropylacrylamide (NIPAM) with a monomer-to-RAFT agent-to-initiator molar ratio of about 600:1:0.2. In certain embodiments, the reaction mixture, without the initiator, is degassed by freeze-pump-thaw. In certain embodiments, the initiator, azobisisobutyronitrile (AIBN), is degassed in a separate solution and added to the reaction mixture immediately before immersing in an oil bath at 65° C. In certain embodiments, the molecular weight of the polymer increases with time, but the reaction is stopped at low conversions (e.g., after 1-2 hours) to keep the polydispersity low. In certain embodiments, the polymer is purified by precipitation in cold ether.

Figure 4:
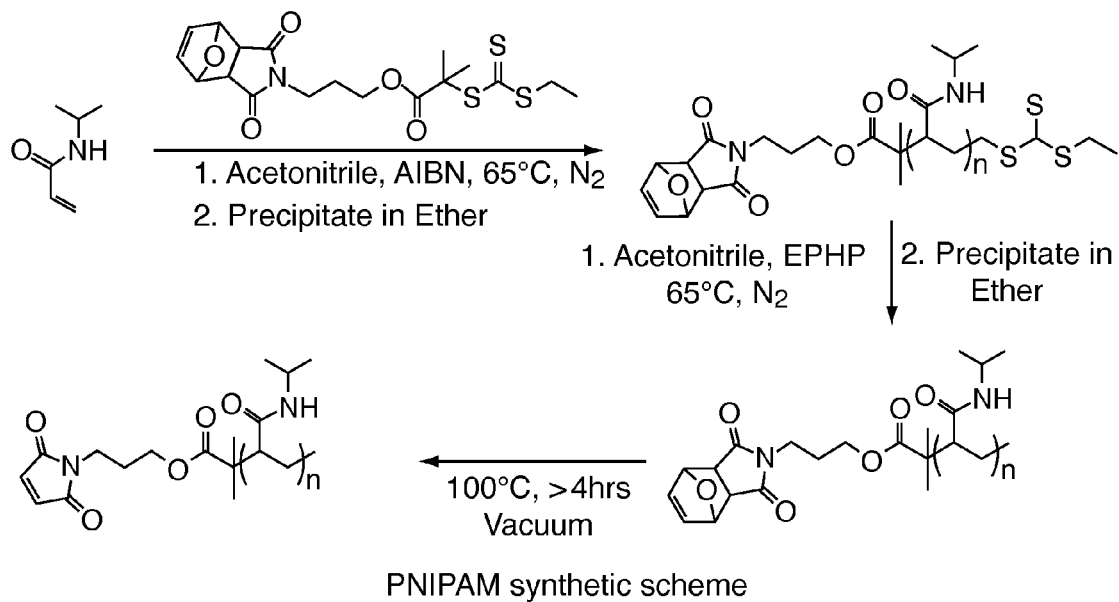
FIG. 4 depicts an exemplary synthetic scheme to PNIPAM.

In certain embodiments, under the conditions of the polymerization and subsequent workup, each polymer contains a single maleimide endgroup. In certain embodiments, as shown in FIG. 4, this maleimide was incorporated into the polymer as a protected group on the RAFT agent. In certain embodiments, prior to deprotection, the trithiocarbonate group, which is incorporated at the other end of the polymer, is removed via a radical induced reduction using N-ethylpiperidine hypophosphite (EPHP) as a hydrogen donor. In certain embodiments, deprotection occurs via a reverse Diels-Alder reaction at 100° C. under vacuum.

Figure 5:
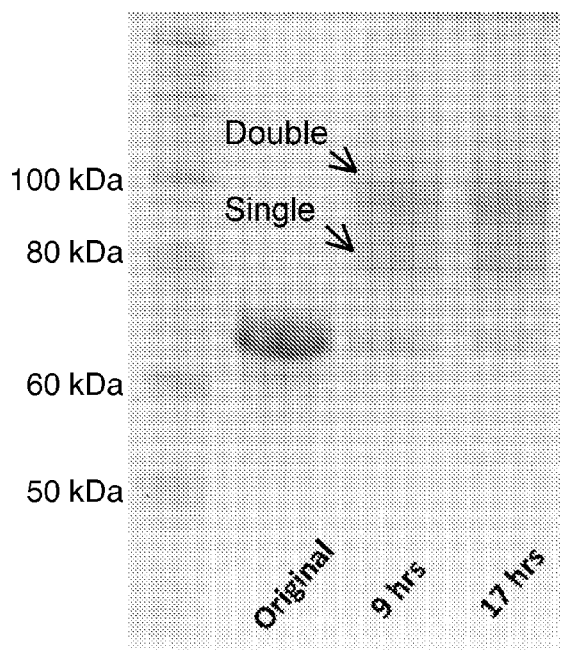
FIG. 5 depicts SDS-PAGE of conjugation of $C_{10}(PC_{10})_2$ to 23 k PNIPAM. Reaction was sampled at 9 h and 17 h, where depletion of the original protein is apparent. A mixture of single and double conjugates is present.

In certain embodiments, the conjugation of maleimide-functionalized PNIPAM to thiol-containing protein occurs under reducing conditions at room temperature. In certain embodiments, the protein is prepared at about 7 mg/mL in a degassed 100 mM phosphate buffer at pH 8 containing 1 mM ethylenediaminetetraacetic acid (EDTA) and 1.3 mM tris(2-carboxyethyl) phosphine. In certain embodiments, the protein is solubilized and reduced overnight at 4° C. In certain embodiments, a 20-fold molar excess of PNIPAM is added to the reduced protein, solubilized at 4° C. for 1 h, and then incubated at room temperature for typically up to 36 h. In certain embodiments, the bioconjugate is purified via Ni-NTA or anionic exchange chromatography under denaturing conditions, and obtained as a lyophilized powder. The efficiency of bioconjugation is shown in FIG. 5.

EXEMPLIFICATION

The invention now being generally described, it will be more readily understood by reference to the following, which is included merely for purposes of illustration of certain aspects and embodiments of the present invention, and is not intended to limit the invention.

Example 1

First Generation Double-Network Physical Gel

Synthesis of the Protein Midblock

Figure 2:
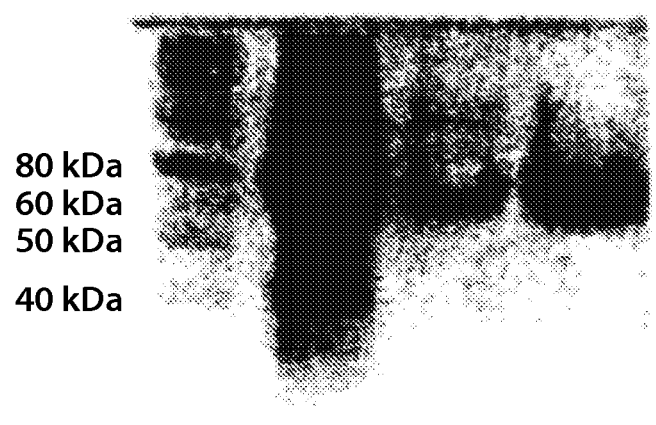
FIG. 2 depicts SDS-PAGE of the purification of thiol-flanked $C_{10}(PC_{10})_2$ proteins. Lanes are labeled as flowthrough (FT), wash (W), and elution (E). Ladder is marked in units of kDa.

The protein midblock was synthesized biologically in *E. coli* and purified from the cell lysate by affinity chromatography. The amino acid sequence was designed based on existing artificial protein hydrogels, as described above. The sequence contains an alternating arrangement of flexible linker domains ($C_{10}$) and associating domains (P) in the order $C_{10}(PC_{10})_2$ and $C_{10}(PC_{10})_4$. The sequence includes exactly two thiol containing cysteine residues, one at each terminus, which are used in subsequent conjugation reactions. The gene was subcloned into the pQE9 expression system from Qiagen, which contains an N-terminal His-tag, enabling purification by Ni-NTA affinity chromatography (FIG. 2). Purification was performed under reducing conditions by the addition of 10 mM 2-mercaptoethanol in all buffers. Protein was recovered as a lyophilized powder.

Synthesis of the PNIPAM Endblocks

A typical polymerization reaction targeting a molecular weight of approximately 30 kDa was performed in acetonitrile at a 2.0 M concentration of N-isopropylacrylamide (NIPAM) with a monomer-to-RAFT agent-to-initiator molar ratio of 600:1:0.2. The reaction mixture, without the initiator, was degassed by freeze-pump-thaw. The initiator, azobisisobutyronitrile (AIBN), was degassed in a separate solution and added to the reaction immediately before immersing in an oil bath at 65° C. The molecular weight of the polymer increased with time, but the reaction was stopped at a low conversion (typically around 40% after 1-2 hours) to keep the polydispersity low. The polymer was purified by precipitation in cold ether.

The trithiocarbonate group, which is incorporated at the other end of the polymer, was removed via a radical induced reduction using N-ethylpiperidine hypophosphite (EPHP) as a proton donor. Deprotection of the maleimide occurred via a simple reverse Diels-Alder reaction at 100° C. under vacuum.

Conjugation

The conjugation of maleimide-functionalized PNIPAM to thiol-containing protein occurred under reducing conditions at room temperature. The protein was prepared at 3 mg/mL in a degassed 100 mM phosphate buffer at pH 8 containing 1 mM ethylenediaminetetraacetic acid (EDTA) and 1.3 mM tris(2-carboxyethyl) phosphine. The protein solubilized and reduced overnight at 4° C. A 20-fold molar excess of PNIPAM was added to the reduced protein, solubilized at 4° C. for 1 h, and then incubated at room temperature for typically up to 36 h. The bioconjugate was purified via Ni-NTA chromatography and obtained as a lyophilized powder. The efficiency of bioconjugation is shown in FIG. 5.

Characterization

Independent assembly of the protein gel and PNIPAM networks has been confirmed by measuring the temperature-dependent linear elastic properties of the gels. Samples were prepared by solubilizing the lyophilized bioconjugate for 2 h at 4° C. in 100 mM phosphate buffer at pH 7.6 at approximately a 14% (w/v) concentration. The material was thermally cycled approximately 10-20 times and repeatedly alternated between a clear viscous liquid at room temperature and a turbid, stiff gel at 37° C. Sample was then thermally cycled between room temperature and 100° C., vortexed, and briefly centrifuged approximately 5 times to attempt form a homogeneous sample.

Figure 6:
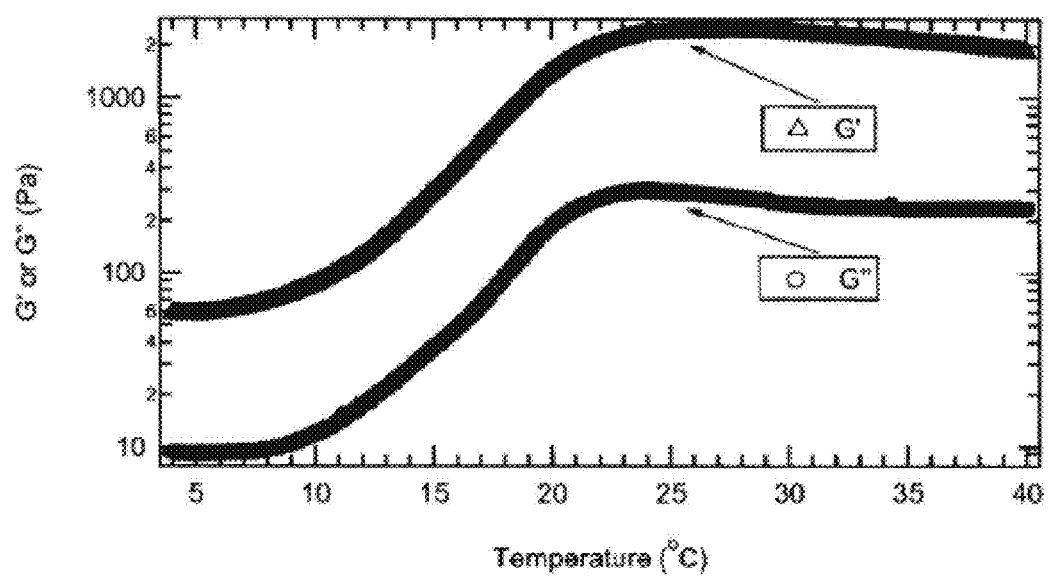
FIG. 6 depicts temperature-sweep linear rheology data of an approximately 7% (w/v) gel, indicating a transition temperature near 15° C.

Rheology was performed on a TA instruments AR2000 oscillatory shear rheometer equipped with a Peltier heating stage. The sample was loaded at 4° C. and measurements were taken using a 20-mm cone geometry. Following an annealing step, two temperature sweeps were performed at a frequency of 1 rad/s, a strain of 10%, and heating/cooling at 0.5° C./min (FIG. 6). Over a 30-fold enhancement in the initial elastic modulus was observed.

Example 2

Figure 7:
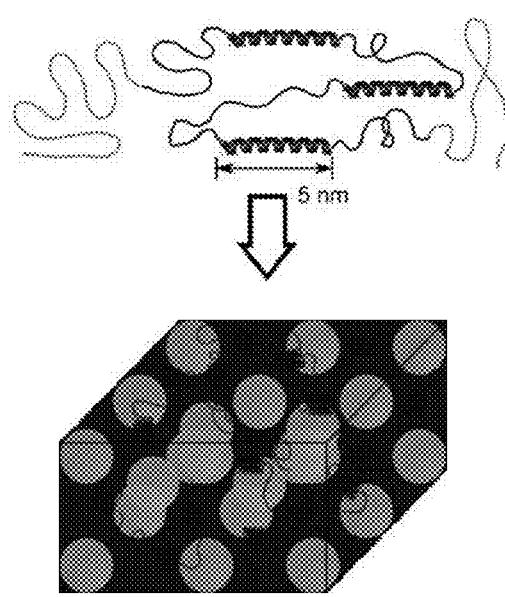
FIG. 7 depicts a molecular architecture, showing coiled-coil associating domains in the midblock and self-assembly of reinforcing polymer domains.
Figure 8:
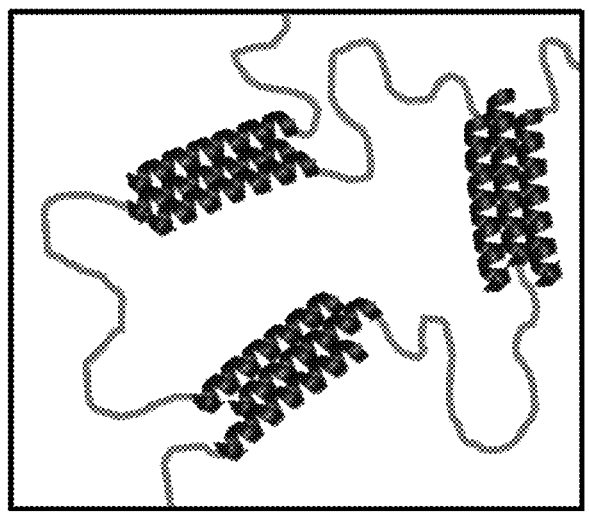
FIG. 8 depicts the network topology of a protein-based shear-thinning injectable hydrogel utilizing coiled-coil associating domains joined by flexible linker domains. In this example, coiled-coils associate anti-parallel with a well-defined valency of three.
Figure 9:
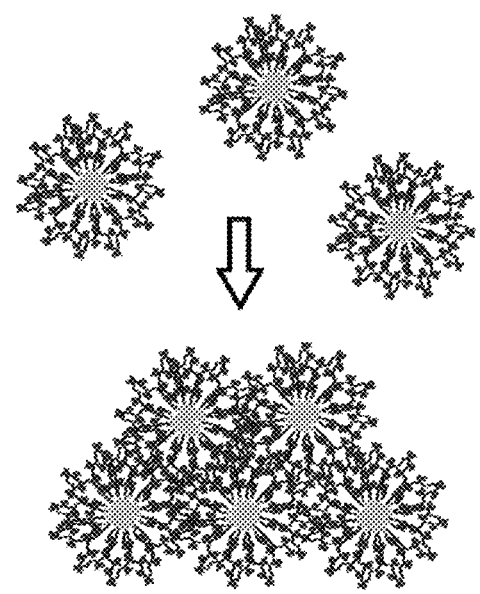
FIG. 9 depicts the aggregation of triblock copolymer micelles to form a network. Hydrophobic endblocks segregate to a dense core and the hydrophilic midblocks adopt extended conformations in solution.

Design, Synthesis, and Demonstration of a Double-Network Physical Gel as a Responsively Tough, Injectable Biomaterial Overview Shear-thinning in protein-based hydrogels made from coiled-coil associating domains makes these materials injectable, but prevents their use in applications requiring high fracture toughness. Any mechanism to toughen these materials must be responsive in order to retain their useful shear-thinning property. Self-assembly of a thermoresponsive polymer into nanodomains dispersed throughout the gel may provide the desired responsive mechanical enhancement in a way that is easily integrated in the clinical setting. A gel-forming protein has been incorporated into the midblock of a symmetric triblock copolymer (FIG. 7). The endblocks are poly(N-isopropylacrylamide) (PNIPAM), which has a lower critical solution temperature (LCST) near 30° C. in water. Thus, upon heating, the PNIPAM endblocks assemble into reinforcing domains dispersed in the gel, forming a double-network architecture.

Material Synthesis

Synthesis of the triblock copolymer was achieved in three steps: (1) cloning and biosynthesis of thiol-flanked gel-forming protein, (2) RAFT agent synthesis and NIPAM polymerization to produce maleimide-functionalized PNIPAM, and (3) thiol-maleimide conjugation and purification.

Figure 10:
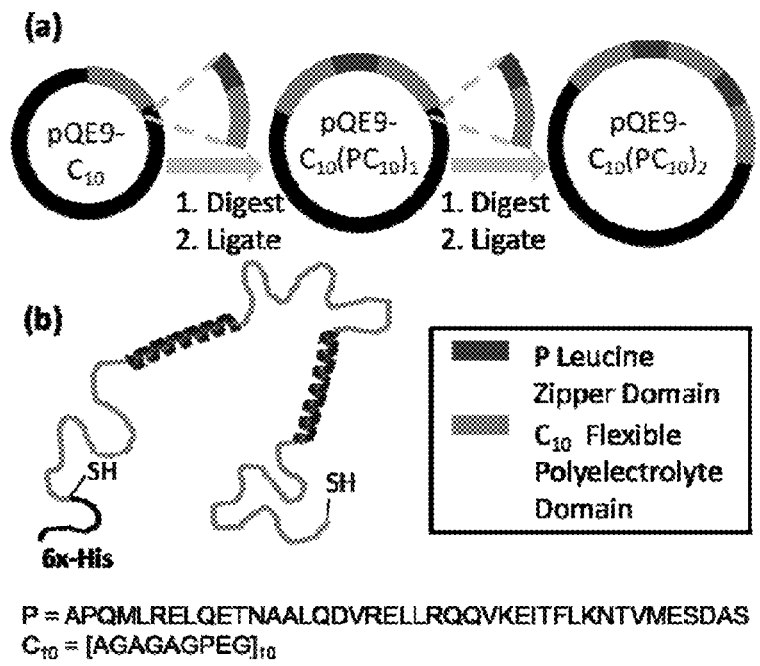
FIG. 10 depicts the design of a gel-forming protein midblock. (a) Schematic for the cloning of $C_{10}(PC_{10})_x$ genes by sequential ligation of $PC_{10}$ sequences. (b) Cartoon of the structure of $C_{10}(PC_{10})_2$ indicating folded leucine zippers, structure-less $C_{10}$ linkers, 6x-histidine affinity tag (SEQ ID NO: 1), and N- and C-terminal thiols.

Four gel-forming proteins were designed that contained one, two, three, or four pentavalent leucine zipper associating domains (abbreviated, P), connected by flexible (i.e. structure-less) polypeptide linker domains (abbreviated, $C_{10}$) in the arrangement $C_{10}(PC_{10})_x$ (see FIG. 10). The sequence is flanked by $C_{10}$ domains to separate the associating domains from the PNIPAM conjugation sites. Cysteine, the only thiol-containing natural amino acid, is absent from the entire sequence, save one near each terminus. The protein sequence contains an N-terminal 6xHis tag (SEQ ID NO: 1), which enables purification via highly specific Ni-NTA affinity chromatography.

Figure 11:
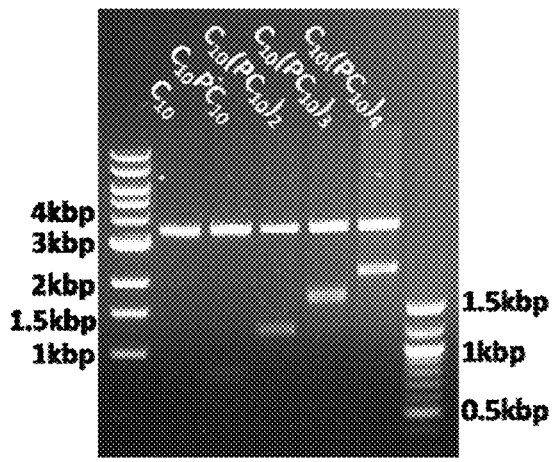
FIG. 11 depicts the restriction digests of completed vectors, indicating successful cloning. The empty vector is 3.3 kbp, and the expected insert sizes—from left to right—are 0.5 kbp, 0.7 kbp, 1.2 kbp, 1.6 kbp, and 2.1 kbp.

Gene synthesis was accomplished by amplifying DNA fragments containing $PC_{10}$ from the $PC_{10}P$ gene in a two-step process using primers that contained NheI and SpeI restriction sites at the 5' and 3' ends, respectively. This fragment was ligated downstream of a $C_{10}$ gene into a SpeI-digested vector to yield $C_{10}PC_{10}$. The NheI/SpeI combination is convenient for sequential ligation because digestion yields identical overhangs from both enzymes, but the 5' NheI recognition sequence is destroyed upon ligation in the proper head-to-tail orientation. Thus, $C_{10}PC_{10}$ contains a single SpeI site near the C-terminus, and after digestion with SpeI, another $PC_{10}$ fragment can be ligated to give the $C_{10}(PC_{10})_2$ gene. All four genes were constructed sequentially in this manner, then inserted into the multiple cloning site (MCS) of a pQE9 expression vector modified to contain a single cysteine on either end of the insertion site. Proper insertion was verified by analytical restriction digests (FIG. 11). The genes were transformed into the SG13009 strain of E. coli for protein expression.

Figure 12:
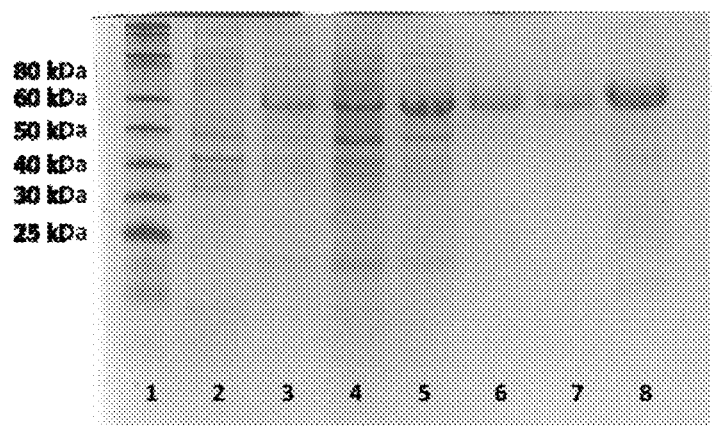
FIG. 12 depicts SDS-PAGE of biosynthesis and purification. (1) Ladder (2) 0 h post-induction (3) 6 h post-induction (4) purification flowthrough (5-7) sequential wash steps (8) elution fraction. The band that runs at approximately 60 kDa is the desired product.

Protein expression began by inoculating a 1 L culture of terrific broth (TB) with 5 mL of an overnight culture. Cells were grown to an OD of 0.9-1.1 and induced with 1 mM isopropyl β-D-1-thiogalactopyranoside (IPTG). Cells were harvested by centrifugation 6 hours post-induction and frozen at −80° C. Cells lysis was completed after two rounds of sonication for 10 minutes in phosphate buffer containing 8 M urea. The clarified lysate was purified by Ni-NTA chromatography and the protein was dialyzed and lyophilized. Typically, yields were between 70-120 mg/L of expression culture, with lower yields for the larger proteins. All purification buffers contained 10 mM β-mercaptoethanol (BME) to maintain the lysate in reducing conditions since disulfide bonds are known to degrade irreversibly at elevated pH. Furthermore, BME improved purity by preventing His-tagged proteins from retaining other thiol-containing proteins from the cell lysate during purification. Purity was assessed by polyacrylamide gel electrophoresis under denaturing conditions (SDS-PAGE) (FIG. 12), and its molecular weight can be quantitatively determined by MALDI-TOF.

Figure 13:
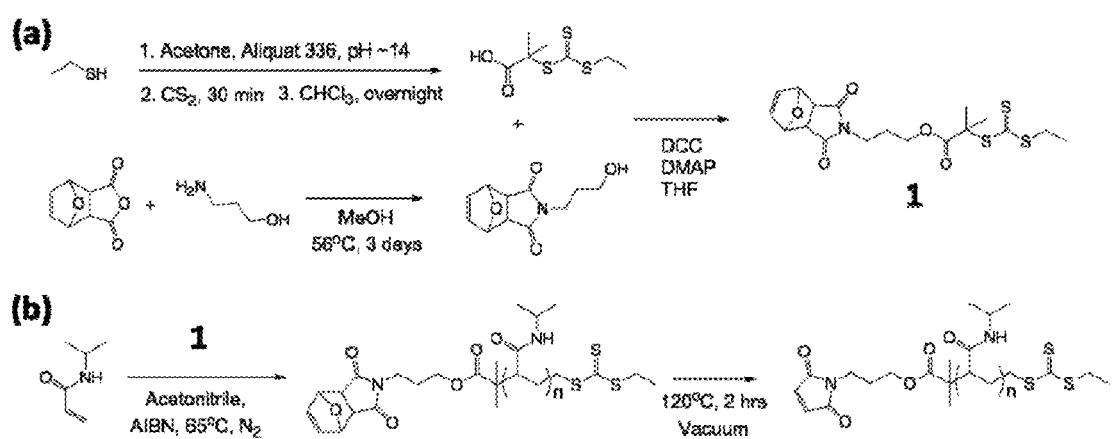
FIG. 13 depicts the (a) synthesis of RAFT CTA with protected maleimide group (1) and (b) subsequent polymerization and deprotection steps.

PNIPAM was synthesized via reversible addition-fragmentation chain transfer (RAFT) polymerization to yield polymers with controlled molecular weight and low polydispersity. RAFT polymerization further enables quantitative incorporation of a broad diversity functional endgroups on the growing polymers, convenient for use in the subsequent protein-conjugation step. The RAFT chain transfer agent (CTA) used in this work was designed to contain a protected maleimide group (FIG. 13). NIPAM was polymerized in acetonitrile in the presence of this CTA, using thermally-labile azobisisobutyronitrile (AIBN) as a radical source. Polymer was recovered by precipitation in ether at −40° C. Conditions can be varied to produce polymers ranging from 15-40 kDa, as measured by gel permeation chromatography (GPC) with a poly(methylmethacrylate) calibration.

Figure 14:
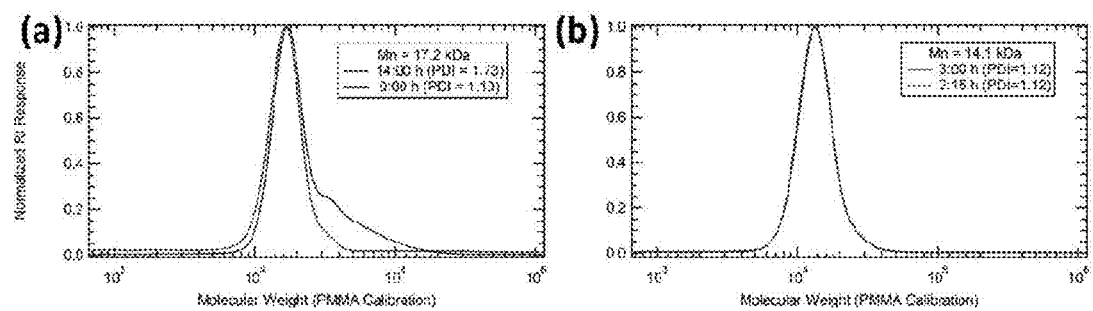
FIG. 14 depicts GPC distributions for two polymers deprotected under different conditions to demonstrate the importance of processing on the quality of the deprotected polymer: (a) after 14 h at 110° C., and (b) solvent removed at RT overnight, then deprotection at 120° C. for up to 3 h.
Figure 15:
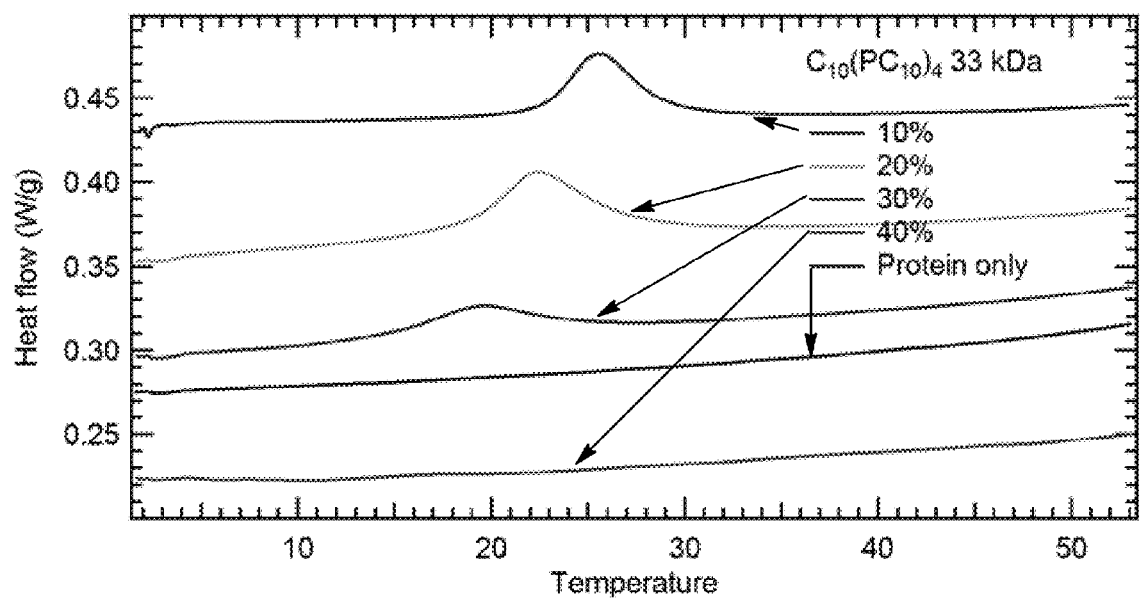
FIG. 15 depicts that reversing heat flow on heating from modulated-temperature differential scanning calorimetry for a concentration series of the protein-polymer conjugate with four associating domains in the midblock and 33 kDa endblocks. The peak in the exotherm is due to the microphase separation of the PNIPAM endblocks. The midblock protein alone shows no features.

Following polymerization, deprotection occurred via a facile reverse Diels Alder reaction at 120° C. under vacuum for 2 hours. This step must be performed after the polymer is completely dried into the glassy state because the unprotected maleimide groups can spontaneously polymerize if the polymer is mobile during deprotection, resulting in a high molecular weight shoulder observable in the GPC trace (FIG. 14).

Thiol-containing protein and maleimide-functionalized PNIPAM spontaneously couple under reducing conditions at elevated pH. The maleimide can react with both deprotonated thiols and amines, but thiol-specificity is achieved at reasonable rates at pH 8. The reaction buffer contained tris(carboxyethylphosphine) (TCEP), a reducing agent that does not contain thiols. The buffer was deoxygenated by sparging with $N_2$ for 30 minutes, and then mixed overnight with the protein in a sealed vessel that has been purged with $N_2$. The protein solution was transferred to another sealed vessel containing polymer, which was solubilized at 4° C. for 30 minutes to limit maleimide hydrolysis prior to initiating the reaction. The reaction was allowed to proceed at room temperature for 24 hours. The final concentration of protein was 3 mg/mL and enough polymer was added to achieve a 10-fold excess per thiol. Conversion was assessed by SDS-PAGE (data not shown).

Because the 6xHis-tag (SEQ ID NO: 1) is retained in the conjugate, it can be purified by Ni-NTA chromatography. Purity was easily assessed by means of fluorescein-labeled PNIPAM added during the binding step. In 8 M urea, the PNIPAM LCST is significantly depressed, and binding must be done at 4° C. overnight. However, recovery using this method has been extremely low, approximately 10%. The low yield is possibly due to the reduced accessibility of the 6xHis-tag (SEQ ID NO: 1) or the slow kinetics of binding at low temperature. Due to the protein's low isoelectric point (the pH at which the protein is electrically neutral), the conjugate can be purified by anion exchange chromatography. QAE-Sephadex, a dextran-based strongly basic anion exchange resin, was used to selectively bind the conjugate under denaturing conditions with 8 M urea, 20 mM Tris, pH 9. The resin was washed with about 4 column volumes of buffer containing 50 mM NaCl, and the conjugate was eluted with buffer containing 150 mM NaCl at pH 6. Purity was assessed qualitatively by turbidity of the wash fractions at 37° C. Typically only the first wash fraction was turbid, but at least two more wash fractions were collected before eluting. The elution fraction was dialyzed and lyophilized. Based on the PMMA-calibrated molecular weight of the PNIPAM and the estimated conversion, near complete recovery of the conjugate has been achieved using this method.

Mechanical and Structural Testing

Figure 16:
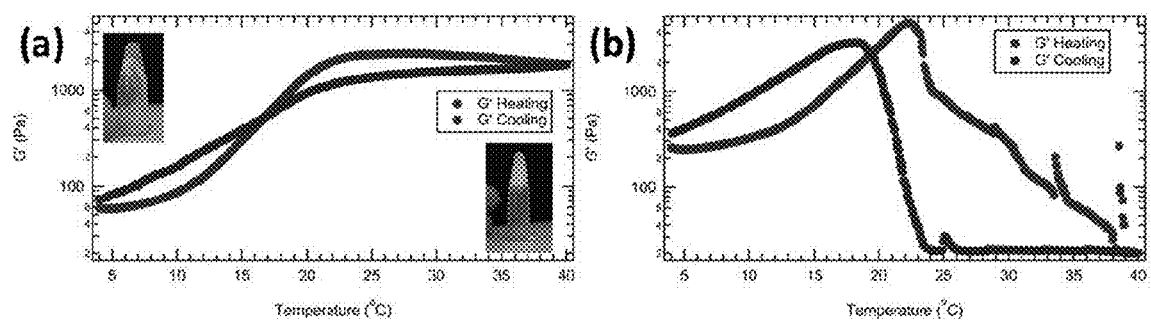
FIG. 16 depicts temperature-sweep linear oscillatory shear rheology demonstrating dynamic evolution of the elastic modulus of (a) a 15% (w/v) sample with 30 kDa endblocks, and (b) a 24% (w/v) sample with 39 kDa endblocks (right). Insets in (a) indicate turbidity change observed upon heating.

Temperature-sweep linear oscillatory shear rheology was used to investigate the change in complex moduli upon assembly of the PNIPAM network. Samples were prepared by hydrating the lyophilized conjugates overnight at 4° C. in 100 mM phosphate buffer, pH 7.6. They were examined in a 20-mm cone and plate geometry using a stress-controlled rheometer. Two representative samples are shown in FIG. 16. The materials were heated at a constant ramp rate (0.5° C./min). The initial gel modulus depended strongly on the overall concentration of material and length of the midblock protein. FIG. 16(*b*) demonstrates a formulation that reconstitutes the modulus of the original protein gel. Both are characterized by an onset of stiffening at a temperature lower than is typically seen in similar materials. However, an important difference between the two samples is the dramatic gel collapse observed in the second sample. Stiffening was observed until about 23° C., well below the LCST of PNIPAM in a similar buffer solution when the modulus steadily drops to zero and percolation in both networks is disrupted.

Figure 17:
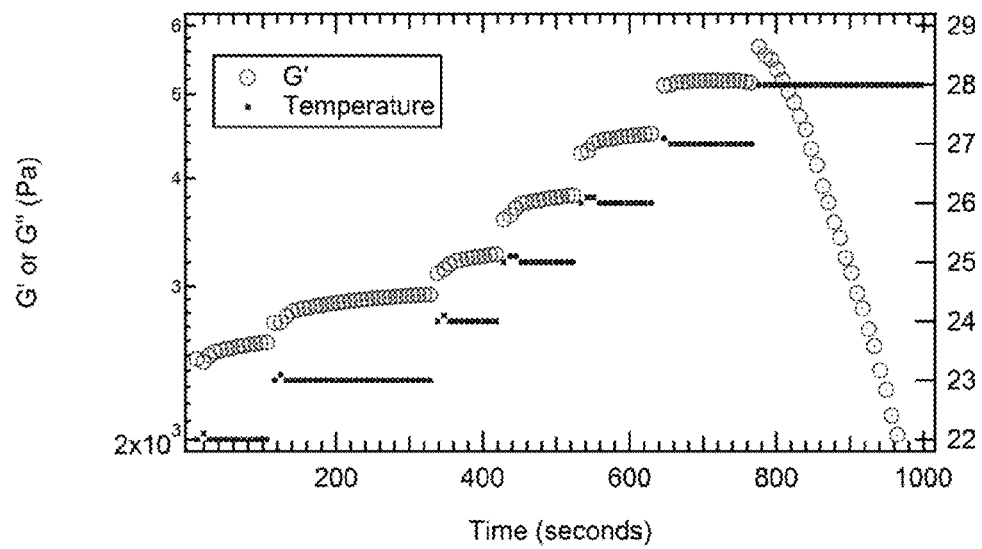
FIG. 17 depicts a stepwise heating program on the conjugate; the data indicates rapid equilibration to new modulus. Onset of gel collapse observed between 27 and 28° C. The right y-axis relates to temperature in ° C.

To develop a better understanding of the dynamic evolution of modulus enhancement and collapse, a sample was subject to a stepwise heating program. Each step-increase in temperature, up to the collapse temperature, resulted in a rapid equilibration to a new modulus (FIG. 17). The only literature study of the dynamics of PNIPAM responsive association in triblock hydrogels observed stiffening over a temperature window of only 5° C., in contrast to the wide temperature range measured for these double-network materials. Kirkland, S. E., et al. *Biomacromolecues* 2007, 9, 481. The stepwise increase in modulus may be explained by either an increase in the strength or number of the PNIPAM physical crosslinks. The strength of the crosslinks may increase due to further exclusion of water from the PNIPAM domains. The number of crosslinks may increase due to inhomogeneities in the protein gel that cause local fluctuations in the PNIPAM concentration, since the LCST is concentration dependent. Upon further heating, the modulus can be seen to dynamically degrade. Network disruption may occur due to phase separation induced by PNIPAM gel formation.

Figure 18:
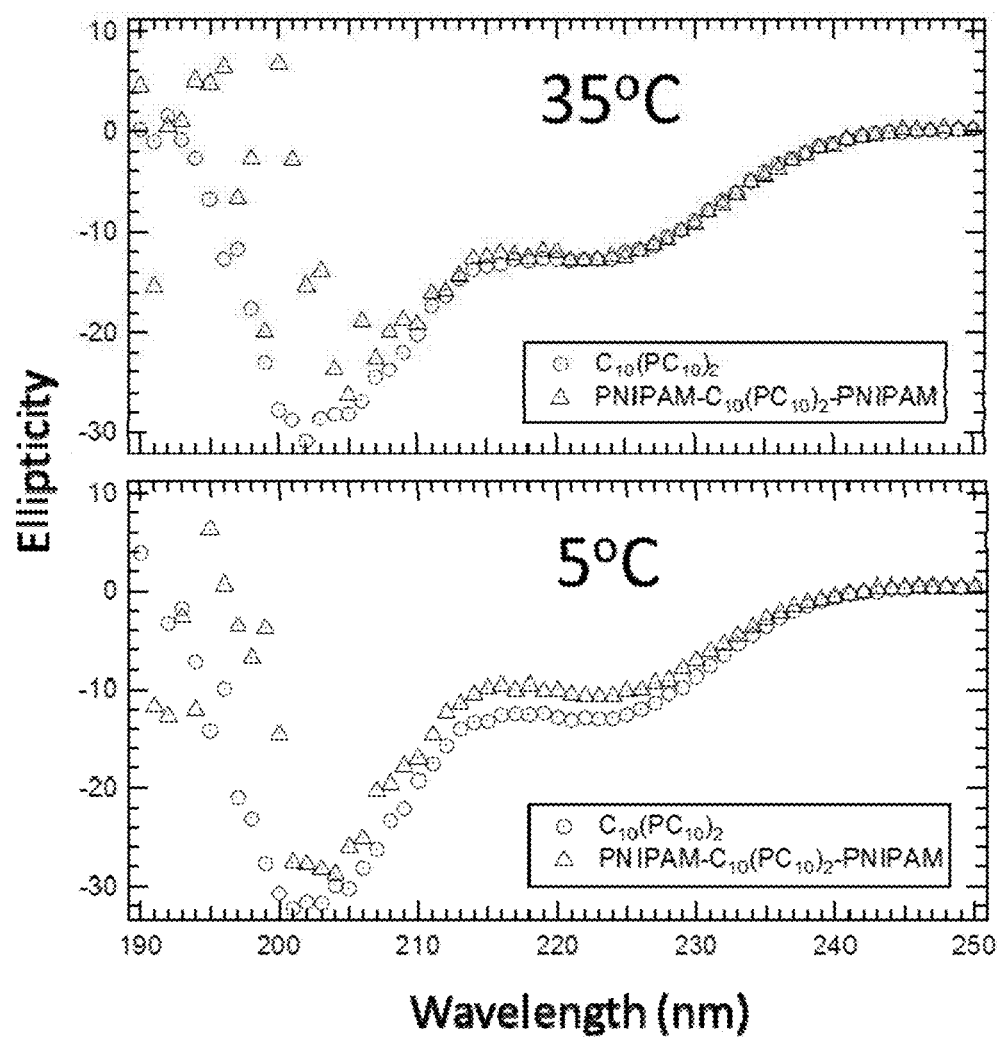
FIG. 18 depicts circular dichroism spectra indicating alpha helical secondary structure (dip in spectrum in the range 210-240 nm) is present above and below the transition temperature.
Figure 19:
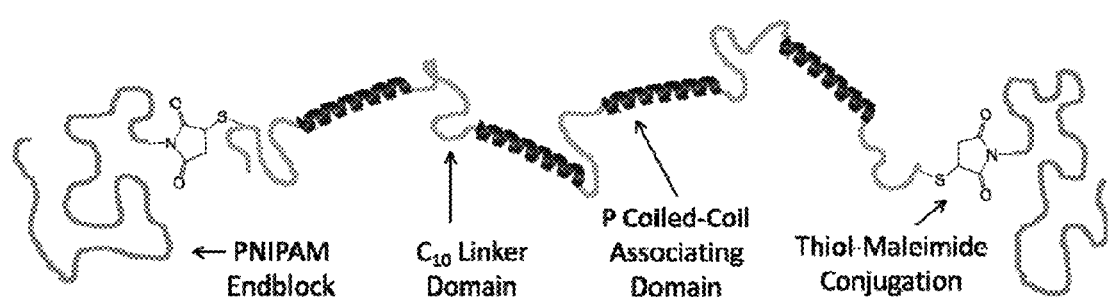
FIG. 19 depicts a schematic representation of a conjugate of the invention.

Mechanical data indicates a complex temperature dependence of network formation, and an understanding of structural transitions is essential to control the responsive mechanical behavior. Dilute solution circular dichroism indicated that the protein's secondary structure is retained both below and above the transition temperature observed in rheological studies (FIG. 18). If the coiled-coil domains retain their fold, they retain their ability to associate. Cryo-SEM revealed features at the appropriate length scales (data not shown), but it appears that vitrification by use of a liquid ethane cryo-plunger will be necessary to reduce artifacts from ice crystals. A preliminary small angle x-ray scattering pattern on a room temperature sample has revealed observable but weak features (data not shown).

Example 3

Improved Protein Synthesis

Overview

Initially, purification of the thiol-flanked self-associating proteins was achieved via metal affinity chromatography using Ni-NTA resin (Qiagen) under reduced, denaturing conditions. Yields were up to 100 mg/L of expression, but were as low as 60 mg/L expression for proteins with a larger fraction of $C_{10}$ blocks. Protein purification by precipitation with chaotropic salts is one alternative method to Ni-NTA purification and is attractive due to its high-throughput capacity and the low cost of materials. The improved protocol involves collecting the fraction of cell lysate that precipitates in a narrow window of ammonium sulfate concentrations (between 20% and 25% w/v) which is remarkably empty of other soluble proteins under the conditions used. Yields were in excess of 175 mg/L expression.

Cloning of Thiol-Flanked Self-Associating, Injectable Proteins

Variants of gel-forming proteins were engineered by alternating the genes of a random coil linker sequence ($C_{10}$) and a pentameric self-associating coiled-coil sequence (P). The genes were cloned with NheI and SpeI recognition sequences at the 5' and 3' ends respectively. Restriction digests with the appropriate enzymes liberate complementary overhangs at both ends, and subsequent ligation yields a single SpeI site at the 3' end when the genes have been cloned in the proper orientation. This strategy was used to sequentially assemble $C_{10}(PC_{10})_4$, $C_{20}(PC_{20})_2$, and $C_{80}$. In a final step, the genes were excised by digestion with NheI and SpeI and inserted into a modified pQE9 expression vector (Qiagen), where the MCS was mutated to include an SpeI recognition sequence flanked by cysteine residues.

Biosynthesis and Purification of Proteins

The genes were transformed into *E. coli* SG13009 with the pREP4 repressor plasmid. 5 mL overnight cultures were used to inoculate 1 L expressions in Terrific Broth. Cells were grown at 37° C. to an optical density of 0.9-1.1 and induced with IPTG at a final concentration of 1 mM. Cells were harvested by centrifugation 6 hours post-induction, and the pellets were stored at −80° C. overnight. For each liter of expression, the cells were resuspended on ice in 50 mL lysis buffer (10 mM Tris, 1 mM EDTA, 100 mM NaCl, pH=7.5, 5 mM $MgCl_2$). 100 mg lysozyme was added, then after 1 hour the suspension was sonicated. Cell debris were removed by centrifugation, and 2 mg each of DNAse I and RNAse A were added to the clarified supernatant and incubated for 2-3 hours at 37° C. Urea (8 M), phosphate (100 mM), and β-mercaptoethanol (BME, 20 mM) were added to the supernatant to denature the lysate. Proteins were purified from the crude lysate by ammonium sulfate precipitation. For $C_{10}(PC_{10})_4$ (P4) and cysteine-flanked $C_{10}(PC_{10})_4$ (cysP4), 10 g of $(NH_4)_2SO_4$ were added per 50 mL buffer, incubated for at least 2 hours, then centrifuged at 37° C. To the supernatant, an additional 2.5 g of $(NH_4)_2SO_4$ was dissolved, the solution incubated, and then centrifuged at 37° C. once more. The cell pellet was resuspended in 8 M urea with 20 mM BME, dialyzed against water, then lyophilized. For cysteine-flanked $C_{80}$ (cysC8), 14 g of $(NH_4)_2SO_4$ were added in the first precipitation, followed by an additional 3.5 g to precipitate the desired protein. Complete digestion of nucleic acids was determined by UV-Vis and protein purity assessed by SDS-PAGE. Yields were typically in excess of 175 mg per liter expression.

Example 4

Improved Synthesis of PNIPAM

Overview

Two important improvements have been made to the PNIPAM synthesis protocol. First, it was determined that the vinyl group on the maleimide-functionalized RAFT agent has a small but noticeable reactivity under the polymerization conditions, resulting in a significant fraction of long-chain branching at high conversions. To produce polymers that are largely free of this branching, as determined by GPC, polymerizations were taken out to no more than 30% conversion. Second, it was determined that additional branching can occur during the high-temperature deprotection step. This was mostly prevented by the addition of free radical inhibitors (such as hydroquinone), or more simply and with higher fidelity, by drying the purified polymer completely—two days under dynamic vacuum—before proceeding with deprotection.

Synthesis of 2-ethylsulfanylthiocarbonylsulfanyl-2-methyl propionic acid (EMP)

Ethanethiol (7.21 mL, 0.1 mol), acetone (73 mL), and tricaprylylmethylammonium chloride (1.0 g, 2.5 mmol) were combined and cooled on an ice bath under $N_2$. Added 9 mL of 50% (w/v) NaOH to the reaction mixture over 10 minutes. After 20 minutes, carbon disulfide (6.03 mL, 0.1 mol) and acetone (12.6 mL) were combined and added dropwise to the reaction over 30 minutes. Chloroform (12 mL, 0.15 mol) was added, followed by the addition of 80 mL of 50% (w/v) NaOH over 10 minutes. The yellow-orange mixture was stirred overnight. Water (200 mL) was added, followed by concentrated HCl (80 mL) to drop the pH below 1. The mixture was extracted three times into diethyl ether and concentrated to a dark red oil. Crude product was purified via silica gel chromatography (1:1 hexanes:ether) and then distilled to yield 11.0 g of a bright orange, viscous liquid (49% yield). $^1$H NMR (CDCl$_3$, δ): 1.33 (t, 3H, —CH$_2$CH$_3$), 1.72 (s, 6H, —C(CH$_3$)$_2$COOH), 3.30 (q, 2H, —CH$_2$CH$_3$).

Synthesis of exo-3a,4,7,7a-tetrahydro-2-(3-hydroxypropyl)-4,7-epoxy-14-isoindole-1,3(2H)-dione (2)

3-amino-1-propanol (4.08 g, 54.2 mmol) added dropwise to a solution of exo-3,6-epoxy-1,2,3,6-tetrahydrophthalic anhydride (9.0 g, 54.2 mmol) in 500 mL methanol. Stirred at 56° C. for 3 days. Reaction mixture was rotovapped to give a clear yellow oil. 100 mL dichloromethane was added and washed three times with 100 mL saturated water. The organic fraction was dried over Na$_2$SO$_4$ and rotavapped to give 2.71 g of a white solid (22% yield). $^1$H NMR (CDCl$_3$, δ): 1.75 (tt, 2H, —CH$_2$(CH$_2$)CH$_2$—), 2.88 (s, 2H, —NC(O)CH—), 3.52 (t, 2H, —NCH$_2$—), 3.65 (t, 2H, —CH$_2$O—), 5.27 (s, 2H, —CH(O)—), 6.52 (s, 2H, —CHCH—).

Synthesis of RAFT CTA with Protected Maleimide (3)

Combined EMP (1.88 g, 8.40 mmol), 2 (1.50 g, 6.72 mmol), 4-dimethylaminopyridine (103.8 mg, 0.84 mmol), and N,N'-dicyclohexylcarbodiimide (3.46 g, 16.8 mmol) in 58 mL dry THF. Stirred at RT under $N_2$ overnight. Filtered and concentrated the reaction mixture. Product was purified from a silica gel chromatography (1:1 hexanes:ethyl acetate) and the second fraction was concentrated into 1.23 g of a bright yellow solid (34% yield). $^1$H NMR (CDCl$_3$, δ): 1.29 (t, 3H, —S—CH$_2$CH$_3$), 1.69 (s, 6H, —C(CH$_3$)$_2$—), 1.85-2.00 (tt, 2H, —CH$_2$(CH$_2$)CH$_2$—), 2.83 (s, 2H, —NC(O)CH—), 3.26 (q, 2H, —CH$_2$CH$_3$), 3.55 (t, 2H, —NCH$_2$—), 4.05 (t, 2H, —CH$_2$O—), 5.24 (s, 2H, —CH(O)—), 6.49 (s, 2H, —CHCH—).

Synthesis of Maleimide-Functionalized PNIPAM Via RAFT

A RAFT chain transfer agent coupled to a protected maleimide functional group was synthesized as described above. To a 2.0 M solution of NIPAM in acetonitrile, the CTA and AIBN were added at a typical molar ratio of 400:1:0.2 (NIPAM:CTA:AIBN). The solution was loaded into a Schlenk flask and degassed by three freeze-pump-thaw cycles. The reaction was immersed in a preheated bath at 55° C. and the extent of polymerization was monitored by GPC. Polymerizations were quenched by opening to air and cooling to room temperature. Polymers were subsequently purified by thermal precipitation in water. First, the acetonitrile was removed via rotary evaporation and the remaining solids were dissolved in excess water at 4° C. overnight. The solution was cold filtered and then centrifuged at 40° C. The polymer was precipitated once more, and then dried completely under vacuum at room temperature. The maleimide endgroup was deprotected at 120° C. for 2 hours under vacuum.

Example 5

Improved Protein-PNIPAM Conjugation

Overview

In early embodiments, the protein-polymer bioconjugate was purified via Ni-NTA affinity chromatography, however this resulted in approximately 10% recovery of bioconjugate per binding step. Near 100% recovery is now achieved using ion exchange chromatography, which has the added benefit of being significantly less expensive. The conjugate is bound to the anionic exchange resin under denaturing conditions at pH=6.5 in a low ionic strength buffer. Excess washing with binding buffer removes the free PNIPAM, as determined by monitoring the washes for the characteristic UV absorbance of the trithiocarbonate group at 310 nm, and the conjugate is eluted with 500 mM sodium chloride.

Bioconjugation

Thiol-maleimide conjugations were performed in 100 mM phosphate buffer, pH=8.0, supplemented with 1 mM EDTA. Tris(2-carboxyethylphosphine) (TCEP) was dissolved in the buffer immediately prior to use, at a 10-fold excess per cysteine. Lyophilized protein (7 mg/mL) and deprotected PNIPAM (10-fold excess per cysteine) were added to the buffer, and the reaction was allowed to proceed overnight at 4° C. with constant stirring. Conjugates were purified from the excess polymer by ion exchange chromatography using QAE-Sepandex A-50 resin (GE Healthcare). The reaction mixture was dialyzed briefly against water to remove the phosphate, then urea (8 M) and Tris (20 mM) were added and the pH adjusted to 6.4. Conjugates were bound to a Sephadex column as slowly as possible. The concentration of PNIPAM in the flowthrough was monitored by UV-Vis, since the trithiocarbonate group on the RAFT agent has a strong absorbance at 310 nm. The resin was washed with excess binding buffer (8 M urea, 20 mM Tris, pH=6.4) until the A310 signal was minimized. Then, conjugates were eluted using binding buffer with 500 mM NaCl. The elutions were dialyzed completely against water and lyophilized.

Example 6

Structural Data: SAXS, SANS, and Birefringence

Overview

Small-angle X-ray and neutron scattering experiments (SAXS and SANS), complimented by birefringence studies, have been undertaken to demonstrate the role of microphase separation in the mechanical enhancement of this thermoresponsive hydrogel. At low concentrations (<20% w/w), structural features were either not observed or were relatively weak in the SAXS patterns for these hydrogels at most temperatures. At moderate concentrations (30-40%), an intense primary peak was observed at low temperatures, indicating microphase separation even prior to PNIPAM demixing and aggregation. For these samples, SAXS and SANS data showed that new structural features at higher q appear with increasing temperature, indicating increased ordering. Birefringence measurements indicated that, upon heating, the PNIPAM responsively self-assembles into cylindrical or lamellar morphologies, which have been shown to play a role in the toughening of hydrogels compared to spherical micelles. At high concentrations (>60%), SAXS shows that the hydrogels self-assemble into ordered structures even at low temperature, and this structure does not change significantly with temperature.

SAXS

Figure 20:
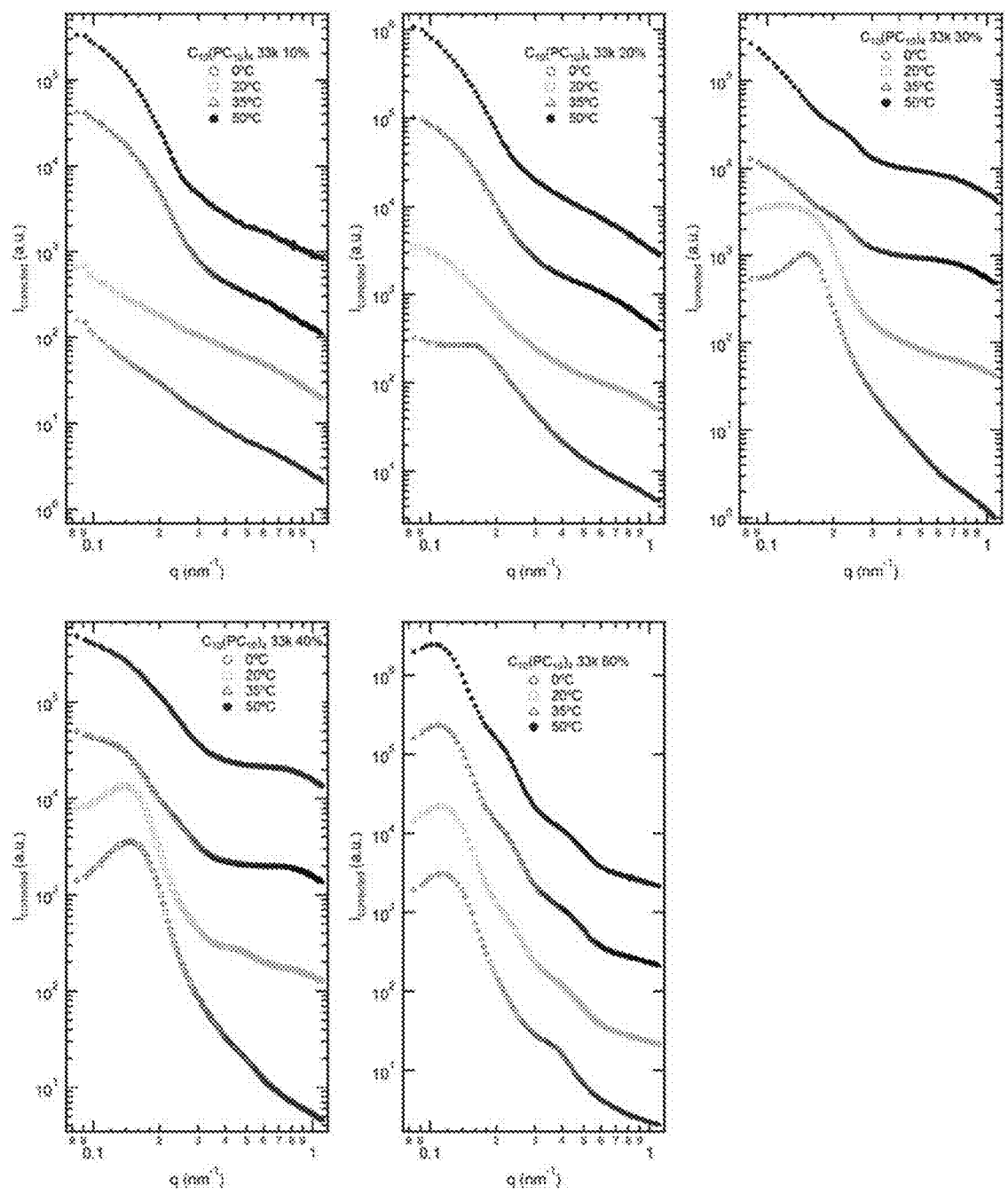
FIG. 20 depicts data from small-angle X-ray scattering at varying concentrations; the endblocks of the polymer tested in these experiments was 33 kDa PNIPAM, and the midblock had four associating domains ($C_{10}(PC_{10})_4$).
Figure 29:
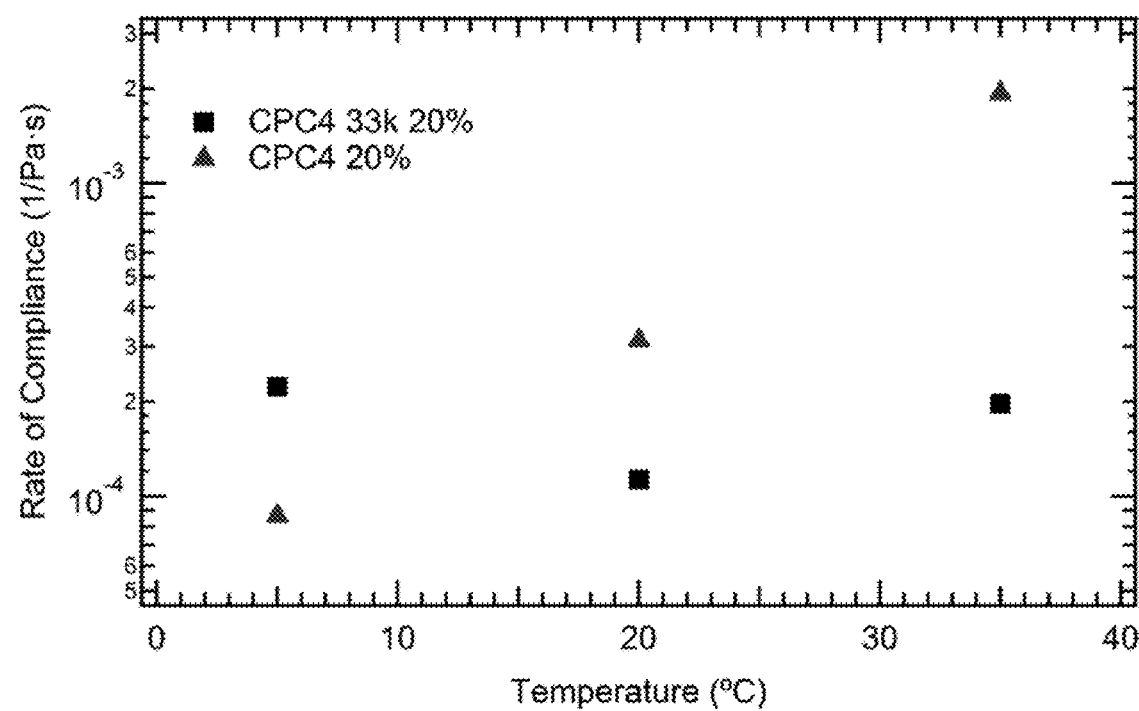
FIG. 29 depicts creep compliance as a function of temperature for a protein-polymer conjugate and a midblock-only hydrogel, which is not thermoresponsively reinforced. Endblock self-assembly leads to an order of magnitude improvement in the creep compliance near body temperature.

Structural information from small-angle scattering provided evidence that the enhancement in modulus and creep compliance (FIG. 29) observed in the thermoresponsive gels is correlated with nanostructure formation. FIG. 20 depicts the concentration dependence of the X-ray scattering features for 33 kDa PNIPAM endblocks and a midblock with four associating domains ($C_{10}(PC_{10})_4$). At low concentrations, only a broad, relatively small increase in intensity at low-q is observed at elevated temperatures. At concentrations higher than 30%, a sharp primary peak is observed in the scattering pattern at low temperature; upon increasing temperature, the intensity of the primary peak decreases while features at higher-q appear. By 60%, the sharp primary peak and higher-q features are present at all temperatures.

SANS

Figure 21:
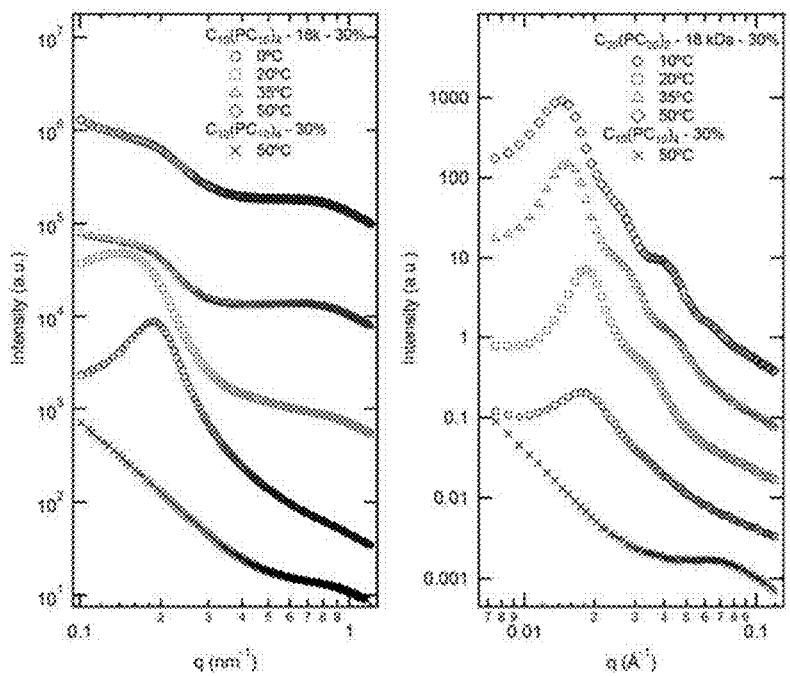
FIG. 21 depicts a comparison of scattering patterns from similar thermoresponsive hydrogels probed by synchrotron X-rays (left) and neutrons (right).

Typically, a decrease in peak intensities is associated with an increase in disorder in a block copolymer system, which would prove difficult to explain given that data from linear oscillatory shear rheology implies that the material self-assembles at higher temperatures. However, because X-ray scattering contrast is low in materials with a high water content, such as these, neutron scattering in deuterated buffers has been explored. FIG. 21 depicts a comparison of scattering patterns from similar thermoresponsive hydrogels, probed by synchrotron X-rays (left) and neutrons (right). The bottom trace in each figure is that of a protein hydrogel alone, which does not contain thermoresponsive endblocks and thus cannot self-assemble. While the X-ray data shows that the primary peak intensity decreases with increasing temperature, the primary neutron scattering peak actually grows at high temperatures, and the appearance of features at higher-q is evident. Thus, even at moderate concentrations scattering indicates that these hydrogels are capable of forming ordered nanostructures.

Birefringence

Figure 22:
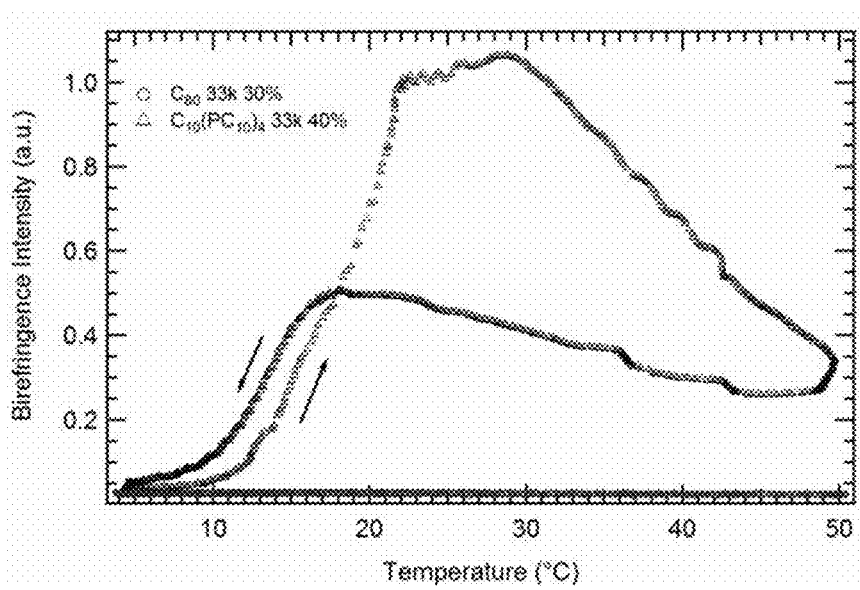
FIG. 22 depicts birefringence data supporting the theory that an exemplary conjugate of the invention self-assembles.

Evidence of the responsive self-assembly of these materials into diverse morphologies is provided by birefringence studies. FIG. 22 shows representative data from two hydrogels: "$C_{80}$ 33 k 30%" has no associating domains in the midblock, 33 kDa endblocks, and is prepared at a 30% concentration, while "$C_{10}(PC_{10})_4$ 33 k 40%" has four associating domains in the midblock, 33 kDa endblocks, and is prepared at a 40% concentration. The onset of birefringence indicates that a sample is able to rotate polarized light due to the formation of cylindrical or lamellar morphologies. These data show that this molecular design provides access to different self-assembled morphologies, which are important for tuning both the responsive mechanical enhancement, and the ability of the hydrogel to interact with living tissue at the nanoscale.

Circular Dichroism Spectroscopy

Characteristic alpha helix trace (FIG. 18) was observed at higher wavelengths; this indicates that the associating domains in the triblock copolymer are folded.

Differential Scanning Calorimetry

Figure 27:
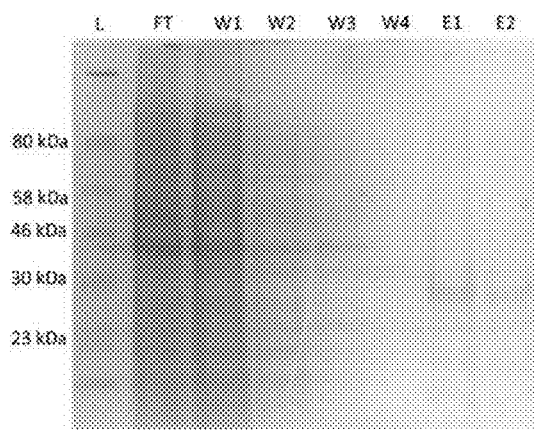
FIG. 27 depicts SDS-PAGE analysis of Ni-NTA Purification of $ELP_5-C_{10}(PC_{10})_4-ELP_5$. Enrichment in His-tagged protein is evident in the elution lanes (E), compared with the purification flowthrough (FT) and washes (W). The expected size is 85 kDa, but these artificial proteins typically run at molecular weights that deviate significantly from common protein markers (L).
Figure 28:
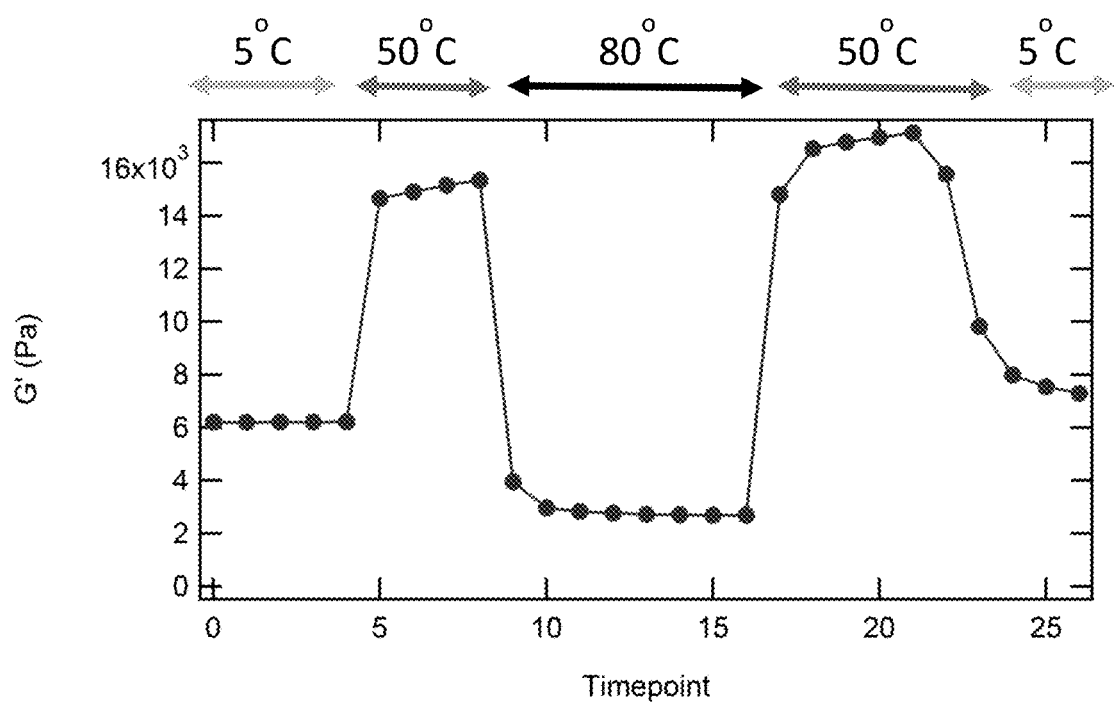
FIG. 28 depicts the results of heating a conjugate of the invention to 80° C. to denature the protein network, thereby revealing the mechanics of the PNIPAM network.

Protein-polymer conjugate showed broad thermal feature near the temperature limit of the hermetically sealed pans. This feature is absent in a hydrogel prepared with protein alone (FIG. 27).

Example 7

Bioconjugates with Alternative Polymer Endblocks

Overview

Figure 25:
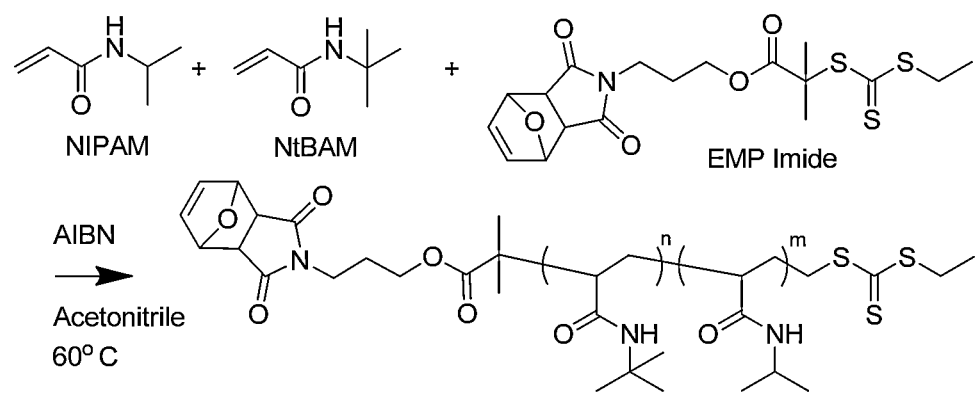
FIG. 25 depicts a synthesis of poly(NIPAM-co-NtBAM) via RAFT.
Figure 26:
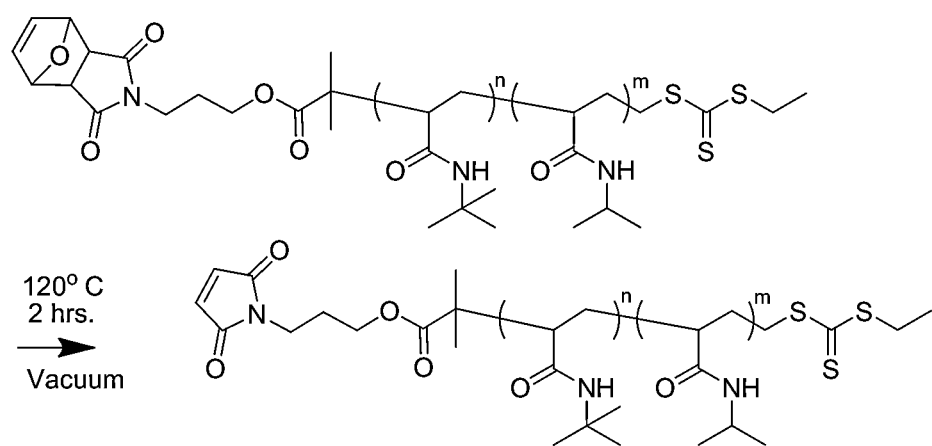
FIG. 26 depicts a synthetic scheme showing deprotection of the EMP imide on the poly(NIPAM-co-NtBAM).

Study of the linear mechanics of the PNIPAM-containing materials revealed that, while the responsive increase in stiffness is complete before 37° C. is reached, the onset of a second characteristic plateau is not complete upon reaching that temperature. This observation is significant because it suggests that the improvement in gel mechanics due to the PNIPAM network, such as increased toughness, may not be fully realized at the intended operating temperature of the material. To resolve this deficiency, maleimide functionalized copolymers of NIPAM and N-tertbutylacrylamide (NtBAM) have been synthesized (FIG. 25). NtBAM is very similar to NIPAM in chemical structure, but an extra methyl group on the side chain makes NtBAM a more hydrophobic monomer, and copolymers with NIPAM have been shown to have decreased lower critical solution temperatures relative the NIPAM homopolymer. Indeed, utilizing these copolymers as endblocks allows the formation of double-network hydrogels that stiffen at lower temperatures and demonstrate the complete onset of a second relaxation time upon reaching body temperature.

Synthesis and Characterization

The main strategy pursued to both lower the LCST and decrease endblock relaxation was copolymerization with a comonomer less hydrophilic than NIPAM. N-tert-butyl acrylamide (NtBAM) was chosen for its structural similarity to NIPAM to preserve the desired thermoresponsive behavior, but an additional methyl component should give NtBAM a lesser degree of solubility in water and thus lead to lower LCST in the copolymer versus NIPAM homopolymer. The ratio of the two monomers influences the LCST, with increasing NtBAM percentage leading to decreasing LCST. Following sublimation of the NtBAM and NIPAM monomers, copolymerization was carried out for determination of effect on LCST. The polymerization was done with maleimide functionalized RAFT agent to allow for conjugation to the protein midblock, synthesized by fellow group members. The ratio of NIPAM to NtBAM was chosen to be 3:1 and 1:1 to target an LCST of roughly 20° C. and 10° C.

After polymerization and purification, it was found that the 3:1 copolymer had a cloud point of about 14° C., while the 1:1 copolymer was simply not soluble in water. Given the effectiveness of LCST suppression, conjugation with the viable poly(NtBAM-co-NIPAM) proceeded. After endgroup deprotection, the maleimide-functionalized copolymer was conjugated to the cysteine residues on the gel-forming protein. The bioconjugate was purified by ion exchange chromatography, dialyzed, and lyophilized. Hydrogels were formed by rehydrating the conjugate in 100 mM phosphate buffer at pH 7.6. Studies of rheology of the complete double network hydrogel are carried out, starting with linear rheology to examine frequency response as a function of temperature. Comparison of elevated temperature frequency sweeps with homopolymer bioconjugates shows a desired change in the relaxation time. Similar rheological behavior was observed at 5° C., with cross over point of the storage and loss moduli starting to shift towards lower frequencies at 20° C. for the copolymer conjugate. The difference at elevated temperatures between the two gels can be seen more clearly, with an earlier onset of the low frequency plateau in storage modulus observed for the copolymer conjugate than for the homopolymer. Large amplitude oscillatory shear rheology was used to examine the yielding behavior of the hydrogels as a function of temperature, but anomalous oscillations in the waveforms indicate that the sample may be experiencing wall-slip at the elevated temperatures.

Example 8

Mechanical Data: Linear Oscillatory Shear Rheology

Overview

Results from linear oscillatory shear rheology indicated that enhancement of the plateau modulus by nearly an order of magnitude is achievable upon heating to body temperature. Frequency sweep rheology demonstrated that the onset of non-terminal behavior (at frequencies as low as 0.003 rad/s) is responsively triggered at temperatures near 50° C. Extremely low frequency relaxation time (<0.003 rad/s) was responsively triggered at temperatures near 50° C. The use of NIPAM-co-NtBAM polymers allows this low frequency relaxation to be triggered by 35° C., making it relevant for use in the body. Furthermore, a decrease in the creep compliance of the responsively stiffened hydrogels is observed compared to hydrogels prepared from the protein midblock alone. Finally, a dramatic decrease in erosion rate of the thermoresponsive hydrogels in the warm state (compared to either the cold state, or a hydrogel prepared from the protein midblock alone) has been observed qualitatively.

Figure 23:
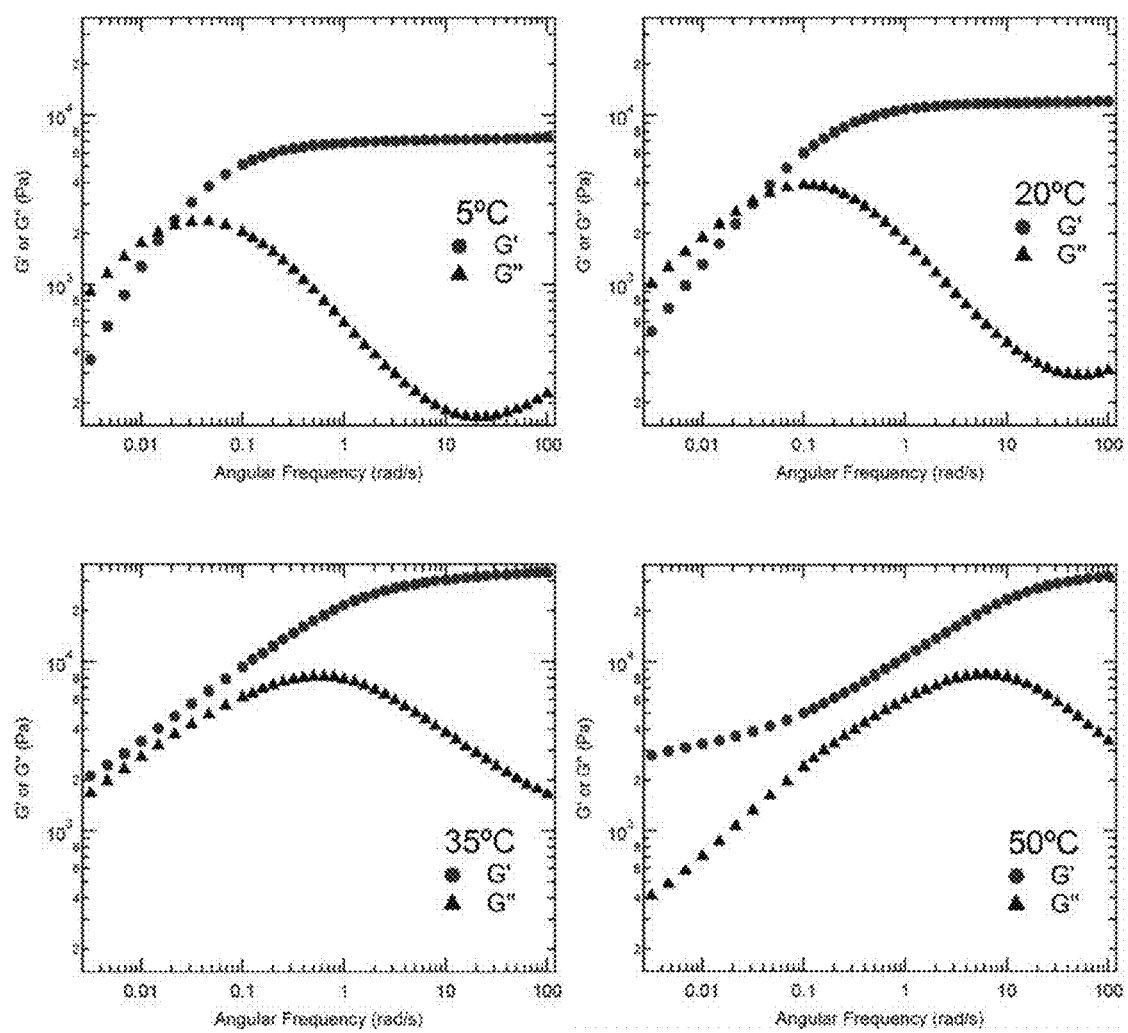
FIG. 23 depicts linear oscillatory shear rheology measurements (storage modulus ($G'(\omega)$) and loss modulus ($G''(\omega)$)) at various temperatures for a conjugate having 18 kDa PNIPAM endblocks on $C_{10}(PC_{10})_4$ at 20% concentration.
Figure 24:
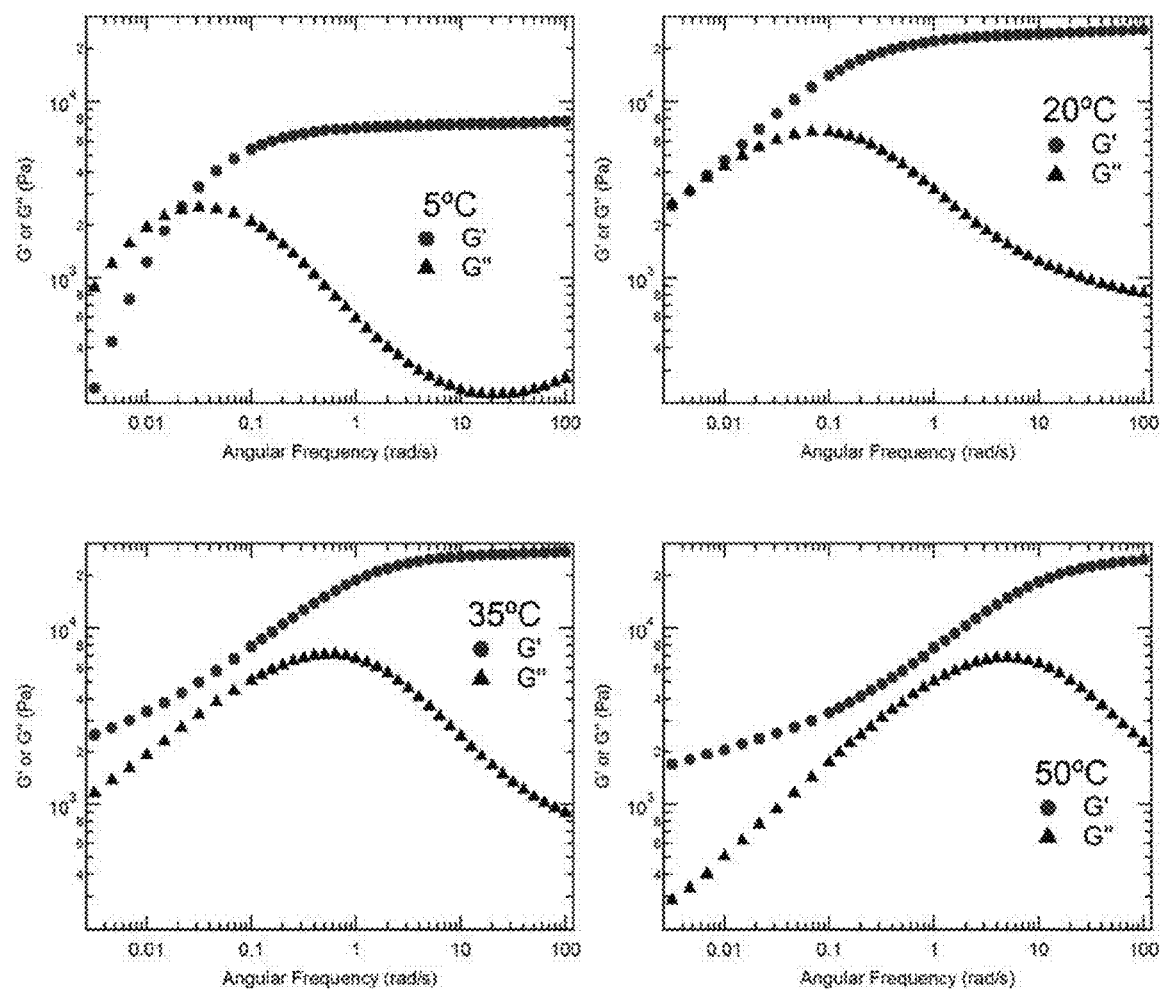
FIG. 24 depicts linear oscillatory shear rheology measurements (storage modulus ($G'(\omega)$) and loss modulus ($G''(\omega)$)) at various temperatures for a conjugate having 18 kDa poly (NIPAM-co-NtBAM) (with approximately 25% NtBAM) endblocks on $C_{10}(PC_{10})_4$ at 17.5% concentration.

Comparison of Conjugates Having PNIPAM Endblocks with Conjugates Having Poly(NIPAM-co-NtBAM) Endblocks The complex moduli of thermoresponsive hydrogels made from (1) PNIPAM endblocks and (2) poly(NIPAM-co-NtBAM) endblocks were measured using linear oscillatory shear rheology. The data in FIG. 23 is for 18 kDa PNIPAM endblocks on $C_{10}(PC_{10})_4$ at a 20% concentration. This data shows two characteristic features of these thermoresponsive gels: a monotinic increase in the plateau modulus at high frequency, and a shift in the crossover point (where G'=G") to higher frequency with increasing temperature. The former effect is due to elastic contributions of the self-assembled PNIPAM domains, and the latter is due to a softening of the protein network associations at elevated temperatures. However one limitation of this current material is that, by 35° C., near body temperature, the plateau modulus is maximized and the onset of non-terminal behavior is evident, but the formation of a second plateau (indicative of long timescale relaxation), is not complete until 50° C.

FIG. 25 depicts data for the copolymer with 25% NtBAM at approximately 18 kDa, attached to $C_{10}(PC_{10})_4$ at a 17.5% concentration. First, the enhancement in elastic modulus was maximized at a lower temperature than in hydrogels made with pure NIPAM endblocks. More importantly, by 35° C., this material was maximally stiffened and the onset of the second relaxation time was essentially complete.

Example 9

Design and Synthesis of a Protein Analog of a Double-Network Physical Gel

A responsively tough, injectable biomaterial made entirely from protein would prove advantageous due to the simplicity and high yield of one-pot biosynthesis, the ability to engineer the primary sequence with absolute precision, and the use of only degradable and biocompatible protein components. To this end, we have designed a fusion of the leucine-zipper based proteins and elastin-like proteins (ELPs) in the same triblock copolymer architecture discussed above. ELPs are known to exhibit LCST-like behavior, and have been presented as an alternative to polypropylene glycol) and poly (butylene glycol)-based Pluronics and Synperonics, which are among the most studied and commercially employed polymeric amphiphiles. ELPs are made from the pentameric polypeptide repeat sequence VPGXG (where X can be any amino acid) (SEQ ID NO: 8), which undergoes a transition from a soluble state to a folded β-hairpin structure at physiologically relevant temperatures. They are particularly useful because the protein fold is tolerant to amino acid substitutions at the fourth position in the pentameric repeat, and decreasing the polarity of this residue can lower the LCST. Furthermore, choosing alanine or glycine in the third position of the repeat can switch the material response from elastomeric to plastic.

Following a strategy similar to that developed by Wright and Conticello, we have designed a scheme to synthesize ADA triblock genes, where our A block is an ELP with a transition temperature of 34.7° C. and the D block is the gel-forming protein utilized in the previous section. Genetic engineering with highly repetitive DNA sequences can be technically challenging because in vitro amplification methods require unique recognition sequences. Furthermore, the high fraction of guanine and cytosine residues in glycine-rich proteins can stabilize secondary structure formation under the reaction conditions, which cause errors during amplification. Therefore, only a single in vitro amplification step has been performed, and the rest of the genetic sequence has been cloned using a combination of in vitro assembly and in vivo amplification.

The A blocks were built by concatemerizing DNA fragments encoding 20 amino acids with the sequence VPAVG (IPAVG)$_4$ (SEQ ID NO: 10). The DNA fragments were cut on both sides with the BspMI restriction enzyme, yielding distinct overhang sequences at the 5' and 3' ends of the fragment. These overhang sequences have been designed so that when mixed in solution the fragments assemble in a head-to-tail orientation via highly-specific base pairing to form larger DNA sequences. The non-covalently assembled sequences were ligated enzymatically to yield concatemerized sequences with a statistical distribution of lengths, depending on the time and temperature of the ligation step. The first concatemers that have been synthesized contain 5 and 8 repeats (11 and 18 kDa respectively), but this strategy provides access to a broad range of protein sizes, including over 30-mer proteins.

Figure 30:
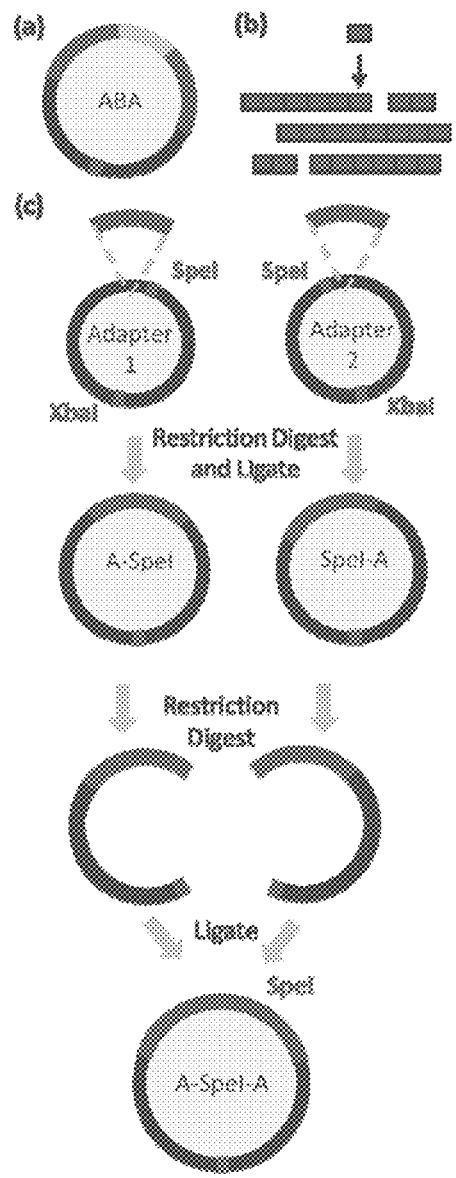
FIG. 30 depicts genetic engineering of ABA triblock copolymers incorporating ELP proteins: (a) Completed gene, (b) Concatemerization to produce large repetetive DNA fragments, (c) Synthesis of A-A construct with internal SpeI site for incorporation of DNA for gel-forming protein.

These concatemers have been ligated into two separate plasmids for in vivo amplification. These two 'adapter' plasmids have been designed so that when they are each digested with the same two restriction enzymes (SeeI and XbaI), they can be ligated together to form a gene with two A blocks flanking the same restriction site (SeeI) (FIG. 30). This site is ideal for integrating the exact gel genes that were previously cloned for the gel-forming midblock. Midblocks of various numbers of associating domains have been integrated into these genes (0, 2, and 4), and future midblock designs are perfectly compatible with both the ELP and PNIPAM-based designs.

Biosynthesis of ELP$_5$-C$_{10}$(PC$_{10}$)$_4$-ELP$_5$ from *E. coli* BL21-DE3 (Qiagen) has been accomplished on the 5 liter scale, and the His-tagged protein has been purified via Ni-NTA affinity chromatography (FIG. 27).

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The invention claimed is:

1. A conjugate comprising a block copolymer of structure A-linker-B(DB)$_x$-linker-A, wherein
   D comprises an associating group, wherein the associating group comprises a sequence of amino acids;
   B represents a flexible second linker group, wherein the flexible second linker group is hydrophilic;
   A represents a polymeric end-group;
   x is 1, 2, 3, 4, 5, 6, 7, 8, 9, or 10; and
   the linker comprises the following structure:

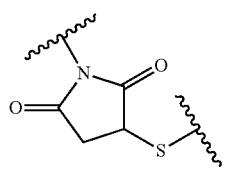

2. The conjugate of claim 1, wherein D is a sequence of from about 30 to about 55 amino acids.

3. The conjugate of claim 1, wherein D is a sequence of about 35, about 36, about 37, about 38, about 39, about 40, about 41, about 42, about 43, about 44, about 45, or about 46 amino acids.

4. The conjugate of claim 1, wherein D is represented by a sequence having at least 85% sequence homology to APQMLRELQETNAALQDVRELLRQQVKEITFLKNTVMESDASG (SEQ ID NO: 2).

5. The conjugate of claim 1, wherein D is represented by a sequence having at least 85% sequence homology to QHIEKSVEEIDEELAKLEEQIKILQTKIEGLVGRHPDLT (SEQ ID NO: 3).

6. The conjugate of claim 1, wherein D is represented by a sequence having at least 85% sequence homology to QHIEKSVEEIDEELAKLEEQKKILQTKREGLVGRHPDLT (SEQ ID NO: 4).

7. The conjugate of claim 1, wherein D is represented by a sequence having at least 85% sequence homology to SGDLENEVAQLEREVRSLEDEAAELEQKVSRLKNEIEDLKAE (SEQ ID NO: 5).

8. The conjugate of claim 1, wherein B is a sequence of from about 70 to about 110 amino acids.

9. The conjugate of claim 1, wherein B is represented by a sequence having at least 85% sequence homology to [AGAGAGPEG]$_{10}$ (SEQ ID NO: 7).

10. The conjugate of claim 1, wherein A is a polymer made from a monomer selected from the group consisting of: N-isopropylacrylamide, N-tert-butylacrylamide, N-isobutylacrylamide, N-octylacrylamide, hydroxypropylacrylate, hydroxyethylacrylate, hydroxymethylacrylate, ethylene glycol acrylate, oligo(ethylene glycol) acrylate, N-isopropylmethacrylamide, methyl methacrylate, ethyl methacrylate, n-propyl methacrylate, isopropyl methacrylate, isobutyl methacrylate, t-butyl methacrylate, methyl 2-furanacrylate, benzyl 2-furanacrylate, vinyl acetate, and stearyl methacrylate, and combinations thereof.

11. The conjugate of claim 1, wherein A is a protein.

12. The conjugate of claim 1, wherein A comprises a sequence of amino acids; the sequence of amino acids comprises a five-amino acid repeat unit; the five-amino acid repeat unit is VPGXG; and X is any amino acid (SEQ ID NO: 8).

13. The conjugate of claim 1, wherein A comprises a sequence of amino acids; the sequence of amino acids is VPAVG(IPAVG)$_4$ (SEQ ID NO: 10).

14. The conjugate of claim 1, wherein A is represented by a sequence of amino acids having at least 85% sequence homology to [VPAVG(IPAVG)$_4$]$_n$; and n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 (SEQ ID NO: 11).

15. The conjugate of claim 1, wherein the number average molecular weight of A is from about 8 kDa to about 50 kDa.

16. The conjugate of claim 1, a wherein A-linker-B is represented by the following structure:

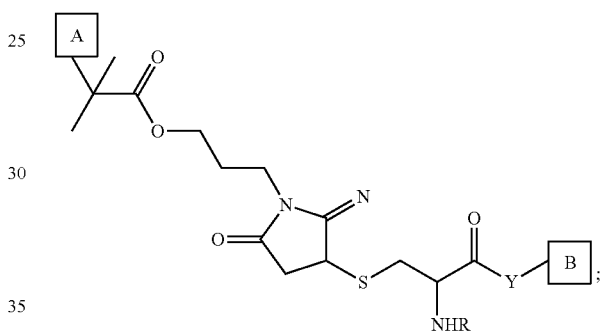

R represents —H or an amino acid; and
Y is absent or an amino acid.

17. The conjugate of claim 1, further comprising a histidine tag.

18. The conjugate of claim 1, wherein x is 1, 2, 3, or 4.

19. A hydrogel, comprising a conjugate of claim 1; and a buffered aqueous solution.

20. The hydrogel of claim 19, wherein the polymeric end-groups are associated with other polymeric end-groups, thereby forming a polymeric end-group network; and the associating groups are associated with other associating groups, thereby forming an associating group network.

21. The hydrogel of claim 19, wherein the hydrogel is a solid at about 37° C. under substantially no shear.

22. The hydrogel of claim 19, wherein the hydrogel is a liquid under shear.

* * * * *

```
                        SEQUENCE LISTING

<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Pro Gln Met Leu Arg Glu Leu Gln Glu Thr Asn Ala Ala Leu Gln
1               5                   10                  15

Asp Val Arg Glu Leu Leu Arg Gln Gln Val Lys Glu Ile Thr Phe Leu
                20                  25                  30

Lys Asn Thr Val Met Glu Ser Asp Ala Ser Gly
            35                  40

<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln His Ile Glu Lys Ser Val Glu Glu Ile Asp Glu Glu Leu Ala Lys
1               5                   10                  15

Leu Glu Glu Gln Ile Lys Ile Leu Gln Thr Lys Ile Glu Gly Leu Val
                20                  25                  30
```

```
Gly Arg His Pro Asp Leu Thr
            35

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln His Ile Glu Lys Ser Val Glu Glu Ile Asp Glu Glu Leu Ala Lys
1               5                   10                  15

Leu Glu Glu Gln Lys Lys Ile Leu Gln Thr Lys Arg Glu Gly Leu Val
            20                  25                  30

Gly Arg His Pro Asp Leu Thr
            35

<210> SEQ ID NO 5
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Gly Asp Leu Glu Asn Glu Val Ala Gln Leu Glu Arg Glu Val Arg
1               5                   10                  15

Ser Leu Glu Asp Glu Ala Ala Glu Leu Glu Gln Lys Val Ser Arg Leu
            20                  25                  30

Lys Asn Glu Ile Glu Asp Leu Lys Ala Glu
            35                  40

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Gly Ala Gly Ala Gly Pro Glu Gly
1               5

<210> SEQ ID NO 7
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Gly Ala Gly Ala Gly Pro Glu Gly Ala Gly Ala Gly Ala Gly Pro
1               5                   10                  15

Glu Gly Ala Gly Ala Gly Ala Gly Pro Glu Gly Ala Gly Ala Gly Ala
            20                  25                  30

Gly Pro Glu Gly Ala Gly Ala Gly Ala Gly Pro Glu Gly Ala Gly Ala
            35                  40                  45
```

```
Gly Ala Gly Pro Glu Gly Ala Gly Ala Gly Ala Pro Glu Gly Ala
        50                  55                  60

Gly Ala Gly Ala Gly Pro Glu Gly Ala Gly Ala Gly Ala Gly Pro Glu
65                  70                  75                  80

Gly Ala Gly Ala Gly Ala Gly Pro Glu Gly
                85                  90

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 8

Val Pro Gly Xaa Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala or Gly

<400> SEQUENCE: 9

Val Pro Gly Xaa Gly
1               5

<210> SEQ ID NO 10
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Pro Ala Val Gly Ile Pro Ala Val Gly Ile Pro Ala Val Gly Ile
1               5                   10                  15

Pro Ala Val Gly Ile Pro Ala Val Gly
            20                  25

<210> SEQ ID NO 11
<211> LENGTH: 800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(800)
<223> OTHER INFORMATION: This sequence may encompass 1-32
      "VPAVG(IPAVG)4" repeating units
```

<400> SEQUENCE: 11

```
Val Pro Ala Val Gly Ile Pro Ala Val Gly Ile Pro Ala Val Gly Ile
1               5                   10                  15

Pro Ala Val Gly Ile Pro Ala Val Gly Val Pro Ala Val Gly Ile Pro
                20                  25                  30

Ala Val Gly Ile Pro Ala Val Gly Ile Pro Ala Val Gly Ile Pro Ala
            35                  40                  45

Val Gly Val Pro Ala Val Gly Ile Pro Ala Val Gly Ile Pro Ala Val
        50                  55                  60

Gly Ile Pro Ala Val Gly Ile Pro Ala Val Gly Val Pro Ala Val Gly
65                  70                  75                  80

Ile Pro Ala Val Gly Ile Pro Ala Val Gly Ile Pro Ala Val Gly Ile
                85                  90                  95

Pro Ala Val Gly Val Pro Ala Val Gly Ile Pro Ala Val Gly Ile Pro
                100                 105                 110

Ala Val Gly Ile Pro Ala Val Gly Ile Pro Ala Val Gly Val Pro Ala
            115                 120                 125

Val Gly Ile Pro Ala Val Gly Ile Pro Ala Val Gly Ile Pro Ala Val
        130                 135                 140

Gly Ile Pro Ala Val Gly Val Pro Ala Val Gly Ile Pro Ala Val Gly
145                 150                 155                 160

Ile Pro Ala Val Gly Ile Pro Ala Val Gly Ile Pro Ala Val Gly Val
                165                 170                 175

Pro Ala Val Gly Ile Pro Ala Val Gly Ile Pro Ala Val Gly Ile Pro
                180                 185                 190

Ala Val Gly Ile Pro Ala Val Gly Val Pro Ala Val Gly Ile Pro Ala
            195                 200                 205

Val Gly Ile Pro Ala Val Gly Ile Pro Ala Val Gly Ile Pro Ala Val
        210                 215                 220

Gly Val Pro Ala Val Gly Ile Pro Ala Val Gly Ile Pro Ala Val Gly
225                 230                 235                 240

Ile Pro Ala Val Gly Ile Pro Ala Val Gly Val Pro Ala Val Gly Ile
                245                 250                 255

Pro Ala Val Gly Ile Pro Ala Val Gly Ile Pro Ala Val Gly Ile Pro
                260                 265                 270

Ala Val Gly Val Pro Ala Val Gly Ile Pro Ala Val Gly Ile Pro Ala
            275                 280                 285

Val Gly Ile Pro Ala Val Gly Ile Pro Ala Val Gly Val Pro Ala Val
        290                 295                 300

Gly Ile Pro Ala Val Gly Ile Pro Ala Val Gly Ile Pro Ala Val Gly
305                 310                 315                 320

Ile Pro Ala Val Gly Val Pro Ala Val Gly Ile Pro Ala Val Gly Ile
                325                 330                 335

Pro Ala Val Gly Ile Pro Ala Val Gly Ile Pro Ala Val Gly Val Pro
                340                 345                 350

Ala Val Gly Ile Pro Ala Val Gly Ile Pro Ala Val Gly Ile Pro Ala
            355                 360                 365

Val Gly Ile Pro Ala Val Gly Val Pro Ala Val Gly Ile Pro Ala Val
        370                 375                 380

Gly Ile Pro Ala Val Gly Ile Pro Ala Val Gly Ile Pro Ala Val Gly
385                 390                 395                 400

Val Pro Ala Val Gly Ile Pro Ala Val Gly Ile Pro Ala Val Gly Ile
```

```
                    405                 410                 415

Pro Ala Val Gly Ile Pro Ala Val Gly Val Pro Ala Val Gly Ile Pro
                420                 425                 430

Ala Val Gly Ile Pro Ala Val Gly Ile Pro Ala Val Gly Ile Pro Ala
                435                 440                 445

Val Gly Val Pro Ala Val Gly Ile Pro Ala Val Gly Ile Pro Ala Val
            450                 455                 460

Gly Ile Pro Ala Val Gly Ile Pro Ala Val Gly Val Pro Ala Val Gly
465                 470                 475                 480

Ile Pro Ala Val Gly Ile Pro Ala Val Gly Ile Pro Ala Val Gly Ile
                485                 490                 495

Pro Ala Val Gly Val Pro Ala Val Gly Ile Pro Ala Val Gly Ile Pro
                500                 505                 510

Ala Val Gly Ile Pro Ala Val Gly Ile Pro Ala Val Gly Val Pro Ala
                515                 520                 525

Val Gly Ile Pro Ala Val Gly Ile Pro Ala Val Gly Ile Pro Ala Val
            530                 535                 540

Gly Ile Pro Ala Val Gly Val Pro Ala Val Gly Ile Pro Ala Val Gly
545                 550                 555                 560

Ile Pro Ala Val Gly Ile Pro Ala Val Gly Ile Pro Ala Val Gly Val
                565                 570                 575

Pro Ala Val Gly Ile Pro Ala Val Gly Ile Pro Ala Val Gly Ile Pro
                580                 585                 590

Ala Val Gly Ile Pro Ala Val Gly Val Pro Ala Val Gly Ile Pro Ala
                595                 600                 605

Val Gly Ile Pro Ala Val Gly Ile Pro Ala Val Gly Ile Pro Ala Val
            610                 615                 620

Gly Val Pro Ala Val Gly Ile Pro Ala Val Gly Ile Pro Ala Val Gly
625                 630                 635                 640

Ile Pro Ala Val Gly Ile Pro Ala Val Gly Val Pro Ala Val Gly Ile
                645                 650                 655

Pro Ala Val Gly Ile Pro Ala Val Gly Ile Pro Ala Val Gly Ile Pro
                660                 665                 670

Ala Val Gly Val Pro Ala Val Gly Ile Pro Ala Val Gly Ile Pro Ala
                675                 680                 685

Val Gly Ile Pro Ala Val Gly Ile Pro Ala Val Gly Val Pro Ala Val
            690                 695                 700

Gly Ile Pro Ala Val Gly Ile Pro Ala Val Gly Ile Pro Ala Val Gly
705                 710                 715                 720

Ile Pro Ala Val Gly Val Pro Ala Val Gly Ile Pro Ala Val Gly Ile
                725                 730                 735

Pro Ala Val Gly Ile Pro Ala Val Gly Ile Pro Ala Val Gly Val Pro
                740                 745                 750

Ala Val Gly Ile Pro Ala Val Gly Ile Pro Ala Val Gly Ile Pro Ala
                755                 760                 765

Val Gly Ile Pro Ala Val Gly Val Pro Ala Val Gly Ile Pro Ala Val
            770                 775                 780

Gly Ile Pro Ala Val Gly Ile Pro Ala Val Gly Ile Pro Ala Val Gly
785                 790                 795                 800

<210> SEQ ID NO 12
<211> LENGTH: 250
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(250)
<223> OTHER INFORMATION: This sequence may encompass 1-10
      "VPAVG(IPAVG)4" repeating units

<400> SEQUENCE: 12

Val Pro Ala Val Gly Ile Pro Ala Val Gly Ile Pro Ala Val Gly Ile
 1               5                  10                  15

Pro Ala Val Gly Ile Pro Ala Val Gly Val Pro Ala Val Gly Ile Pro
            20                  25                  30

Ala Val Gly Ile Pro Ala Val Gly Ile Pro Ala Val Gly Ile Pro Ala
        35                  40                  45

Val Gly Val Pro Ala Val Gly Ile Pro Ala Val Gly Ile Pro Ala Val
    50                  55                  60

Gly Ile Pro Ala Val Gly Ile Pro Ala Val Gly Val Pro Ala Val Gly
65                  70                  75                  80

Ile Pro Ala Val Gly Ile Pro Ala Val Gly Ile Pro Ala Val Gly Ile
                85                  90                  95

Pro Ala Val Gly Val Pro Ala Val Gly Ile Pro Ala Val Gly Ile Pro
            100                 105                 110

Ala Val Gly Ile Pro Ala Val Gly Ile Pro Ala Val Gly Val Pro Ala
        115                 120                 125

Val Gly Ile Pro Ala Val Gly Ile Pro Ala Val Gly Ile Pro Ala Val
    130                 135                 140

Gly Ile Pro Ala Val Gly Val Pro Ala Val Gly Ile Pro Ala Val Gly
145                 150                 155                 160

Ile Pro Ala Val Gly Ile Pro Ala Val Gly Ile Pro Ala Val Gly Val
                165                 170                 175

Pro Ala Val Gly Ile Pro Ala Val Gly Ile Pro Ala Val Gly Ile Pro
            180                 185                 190

Ala Val Gly Ile Pro Ala Val Gly Val Pro Ala Val Gly Ile Pro Ala
        195                 200                 205

Val Gly Ile Pro Ala Val Gly Ile Pro Ala Val Gly Ile Pro Ala Val
    210                 215                 220

Gly Val Pro Ala Val Gly Ile Pro Ala Val Gly Ile Pro Ala Val Gly
225                 230                 235                 240

Ile Pro Ala Val Gly Ile Pro Ala Val Gly
                245                 250

<210> SEQ ID NO 13
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Pro Gln Met Leu Arg Glu Leu Gln Glu Thr Asn Ala Ala Leu Gln
 1               5                  10                  15

Asp Val Arg Glu Leu Leu Arg Gln Gln Val Lys Glu Ile Thr Phe Leu
            20                  25                  30

Lys Asn Thr Val Met Glu Ser Asp Ala Ser
        35                  40
```